(12) United States Patent  (10) Patent No.: US 8,268,823 B2
Leach et al.  (45) Date of Patent: Sep. 18, 2012

(54) MEDICAL USE OF TRIAZINE DERIVATIVES

(75) Inventors: Michael Leach, Kent (GB); Laurence Harbige, Kent (GB); Dieter Riddall, Kent (GB); Paul Barraclough, Kent (GB)

(73) Assignee: University of Greenwich, London (GB)

( * ) Notice: Subject to any disclaimer, the term of this patent is extended or adjusted under 35 U.S.C. 154(b) by 601 days.

(21) Appl. No.: 12/373,561

(22) PCT Filed: Jul. 13, 2007

(86) PCT No.: PCT/GB2007/050405
§ 371 (c)(1),
(2), (4) Date: Mar. 25, 2009

(87) PCT Pub. No.: WO2008/007149
PCT Pub. Date: Jan. 17, 2008

(65) Prior Publication Data
US 2009/0291954 A1 Nov. 26, 2009

(30) Foreign Application Priority Data
Jul. 13, 2006 (GB) .................................. 0613836.6

(51) Int. Cl.
*A61K 31/53* (2006.01)
(52) U.S. Cl. ......................... 514/242; 514/921; 514/821
(58) Field of Classification Search ........................ None
See application file for complete search history.

(56) References Cited

U.S. PATENT DOCUMENTS
4,486,354 A * 12/1984 Baxter et al.

FOREIGN PATENT DOCUMENTS
| EP | 0021120 | 1/1981 |
| EP | 0059 987 | 9/1982 |
| EP | 0142 306 | 5/1985 |
| EP | 0459829 | 12/1991 |
| GB | 759 014 | 10/1956 |
| WO | WO03/008393 | 1/2003 |

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Patani et al., "Bioisosterism: A Rational Approach in Drug Design", Chem. Rev., 1996, vol. 96, pp. 3147-3176.*
Ulomskii et al. "A new approach to the synthesis of lamotrigine and other 3,5-diamino-1,2,4-triazine derivatives" Russian Chemical Bulletin, 54(3):726-732, 2005 XP019224585.
Manning et al. "Synthesis of stable isptopically labelled versions of lamotrigine and its methylated metabolite" J. Label COMPD Radiopharm, vol. 45, 2002, pp. 611-618.

* cited by examiner

*Primary Examiner* — James D Anderson
*Assistant Examiner* — Gregg Polansky
(74) *Attorney, Agent, or Firm* — Occhiuti Rohlicek & Tsao LLP

(57) ABSTRACT

Compounds of formula (I) especially where $R^1$ is an optionally substituted alkyl, aralkyl or heterocyclyl-alkyl group, are shown to have activity as sodium channel blockers or as antifolates. Some novel compounds where $R^1$ is an aralkyl or heterocyclyl-alkyl are disclosed.

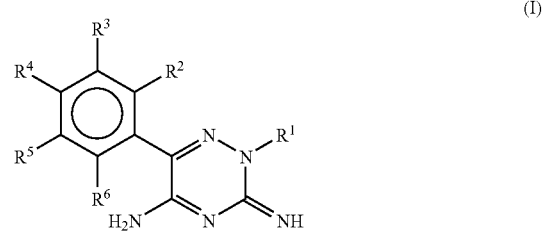

4 Claims, No Drawings

MEDICAL USE OF TRIAZINE DERIVATIVES

CROSS-REFERENCE TO RELATED APPLICATIONS

This application is the National Stage of International Application No. PCT/GB2007/050405 filed Jul. 13, 2007, which claims the priority of British Application No. GB 0613836.6, filed on Jul. 13, 2006. The contents of both applications are hereby incorporated by reference in their entirety.

The present invention relates to the use of triazine compounds as sodium channel blockers and antifolates and for preparation of medicaments for treatment of associated disorders.

U.S. Pat. No. 4,649,139 discloses compounds of the formula (A):

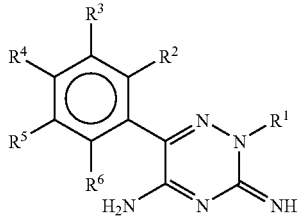

in which $R^1$ is $C_{1-10}$ alkyl, $C_{2-10}$ alkenyl, $C_{2-10}$ alkynyl or $C_{3-10}$ cycloalkyl, any of which is optionally substituted, and $R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups or any adjacent two of $R^2$ to $R^6$ are linked to form a (—CH═CH—CH═CH—) group. It is disclosed that these compounds are active in the treatment of cardiac disorders, and are particularly useful in the treatment of arrhythmias.

The present invention is based on the finding that compounds within formula (A) and certain novel derivatives thereof are potent sodium channel blockers and so are indicated to be useful as voltage dependent sodium channel blockers in treating disorders in mammals and particularly of value in the treatment of epilepsy, multiple sclerosis, glaucoma and uevitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias. Some compounds also show antifolate activity and so are indicated as of value as antifolates for the treatment of mammalian cancers and as antimalarials against *plasmodium vivax* and *plasmodium falciparum* malaria.

Accordingly, the present invention provides use of a compound of formula (I):

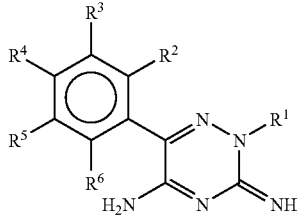

or a salt or solvate thereof in which
$R^1$ is hydrogen, $C_{1-10}$ alkyl, $C_{2-10}$ alkenyl, $C_{1-3}$ alkyl-aryl, $C_{1-3}$ alkyl-heterocyclyl, or $C_{3-10}$ cycloalkyl, any of which is optionally substituted by halogen, halo $C_{1-6}$ alkyl, $C_{1-6}$ alkyl or $C_{1-6}$ alkoxy;

$R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups;

(a) as voltage dependent sodium channel blockers for the treatment of disorders in mammals, and particularly epilepsy, multiple sclerosis, glaucoma and uevitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias, especially in humans;

(b) as antifolates for the treatment of disorders in mammals, and particularly for treatment of mammalian cancers and as antimalarials against *plasmodium vivax* and *plasmodium falciparum* malaria, especially in humans.

The invention further includes the use of compounds of formula (I) for the preparation of a medicament for use as a sodium channel blocker or as an antifolate or as an antimalarial, especially for treatment of the individual disorders mentioned above.

As a $C_{1-10}$ alkyl group, $R^1$ is suitably an unsubstituted $C_{1-6}$ alkyl group, typically methyl, ethyl, i-propyl, n-propyl, i-butyl or n-butyl.

As a $C_{2-10}$ alkenyl group, $R^1$ may be an unsubstituted $C_{2-6}$ alkenyl group, such as allyl.

As a $C_{3-10}$ cycloalkyl group, $R^1$ is typically cyclohexyl, optionally substituted by one or more halogen, haloalkyl or alkoxy groups, for example chloro, fluoro, trifluoromethyl, methoxy or ethoxy.

As a $C_{1-3}$ alkylaryl group, $R^1$ is typically benzyl in which the phenyl group is optionally substituted by one or more halogen, haloalkyl or alkoxy groups, for example chloro, fluoro, trifluoromethyl, trifluoromethoxy, methoxy or ethoxy.

As a $C_{1-3}$ alkyl-heterocyclyl, $R^1$ is suitably piperidine-methyl, optionally N-substituted, or thienyl-methyl, or furyl-methyl.

The $R^2$ to $R^6$-substituted phenyl ring suitably contains one, two or three substituents.

$R^2$ to $R^6$ when other than hydrogen are preferably selected from halogen, halo $C_{1-6}$ alkyl or $C_{1-7}$ alkoxy groups. Particularly preferred substitutions are 2,3 or 2,4 or 2,5 or or 3,5 or 2,3,5 di- or tri-halo (especially chloro and/or fluoro).

In a preferred class of compounds, $R^1$ is not hydrogen.
In another preferred class of compounds, $R^2$ is not hydrogen.
In a further preferred class of compounds, both $R^1$ and $R^2$ are not hydrogen.
In a preferred class of compounds of formula (I):
$R^1$ is $C_{1-10}$ alkyl, $C_{2-10}$ alkenyl, $C_{1-3}$ alkyl-aryl or $C_{1-3}$ alkyl-heterocyclyl, any of which is optionally substituted by halogen, halo $C_{1-6}$ alkyl, $C_{1-6}$ alkyl or $C_{1-6}$ alkoxy; and
$R^2$ to $R^6$ are independently selected from hydrogen and halogen.

In a favoured group of compounds having neuroprotective properties, $R^1$ is $C_{1-4}$ alkyl, optionally substituted by $CF_3$, for example methyl, ethyl, n-propyl, iso-butyl, n-butyl and trifluoropropyl, and $R^2$ and $R^3$, or $R^2$ and $R^4$, or $R^2$ and $R^5$, or $R^3$ and $R^5$, or $R^2$, $R^3$ and $R^5$ are halo, especially chloro and/or fluoro.

Within formula (I) there is a group of compounds in which $R^1$ is hydrogen and to $R^6$ are independently selected from hydrogen, halogen, haloalkyl and haloalkoxy.

Within formula (I) there is a group of compounds in which $R^1$ is alkyl, hydroxyalkyl, haloalkyl, heterocyclylalkyl, alkenyl, carboxamido, benzyl, benzyl substituted by halogen, alkyl, alkoxy, hydroxyalkyl, haloalkyl or carboxamido and to $R^6$ are independently selected from hydrogen and halogen.

Within formula (I) there is a group of compounds in which $R^2$ to $R^6$ are hydrogen and $R^1$ is hydrogen or alkyl Compounds of formula (I) which are novel form a further aspect of this invention.

In particular, compounds of formula (I) in which $R^1$ is optionally substituted $C_{1-3}$ alkyl-heterocyclyl or optionally substituted $C_{1-3}$ alkyl-aryl (excluding unsubstituted benzyl) are believed to be novel compounds.

Illustrative compounds of formula (I) are
5-amino-6-(2,3-dichlorophenyl)-2,3-dihydro-3-imino-2-isopropyl-1,2,4-triazine;
5-amino-6-(2,3-dichlorophenyl)-2,3-dihydro-3-imino-2-n-propyl-1,2,4-triazine;
5-amino-6-(2-pentyloxphenyl)-2,3-dihydro-3-imino-2-methyl-1,2,4-triazine;
5-amino-6-(2,3,5-trichlorophenyl)-2,3-dihydro-3-imino-2-methyl-1,2,4-triazine;
5-amino-6-(2,3-dichlorophenyl)-2,3-dihydro-3-imino-2-methyl-1,2,4-triazine; and
5-amino-6-(2,3-dichlorophenyl)-2,3-dihydro-3-imino-2-benzyl-1,2,4-triazine;

Further compounds of formula (I) include:
5-amino-6-(2,3-dichlorophenyl)-2,3-dihydro-3-imino-2-ethyl-1,2,4-triazine;
5-amino-6-(2,3-dichlorophenyl)-2,3-dihydro-3-imino-2-isopropyl-1,2,4-triazine;
5-amino-6-(2,3-dichlorophenyl)-2,3-dihydro-3-imino-2-n-propyl-1,2,4-triazine;
5-amino-6-(2,3-dichlorophenyl)-2,3-dihydro-3-imino-2-isobutyl-1,2,4-triazine;
5-amino-6-(2,3-dichlorophenyl)-2,3-dihydro-3-imino-2-n-butyl-1,2,4-triazine;
5-amino-6-(2,3-dichlorophenyl)-2,3-dihydro-3-imino-2-allyl-1,2,4-triazine;
5-amino-6-(2,3,5-trichlorophenyl)-2,3-dihydro-3-imino-2-methyl-1,2,4-triazine;
5-amino-6-(2,3,5-trichlorophenyl)-2,3-dihydro-3-imino-2-propyl-1,2,4-triazine;
5-amino-6-(2-fluoro,3-chlorophenyl)-2,3-dihydro-3-imino-2-methyl-1,2,4-triazine;
5-amino-6-(2,3-dichlorophenyl)-2,3-dihydro-3-imino-2-(3,3-trifluoropropyl)-1,2,4-triazine;
5(3)-amino-6-(2,4-dichlorophenyl)-2,3(2,5)-dihydro-3(5)-imino-2-methyl-1,2,4-triazine;
5(3)-amino-6-phenyl-2,3(2,5)-dihydro-3(5)-imino-2-methyl-1,2,4-triazine;
5(3)-amino-6-phenyl-2,3(2,5)-dihydro-3(5)-imino-2-ethyl-1,2,4-triazine;
5(3)-amino-6-(2,5-dichlorophenyl)-2,3(2,5)-dihydro-3(5)-imino-2-methyl-1,2,4-triazine;
5(3)-amino-6-(2,5-dichlorophenyl)-2,3(2,5)-dihydro-3(5)-imino-2-ethyl-1,2,4-triazine;
5(3)-amino-6-(2,3,5-trichlorophenyl)-2,3(2,5)-dihydro-3(5)-imino-2-ethyl-1,2,4-triazine;
5(3)-amino-6-(2,3-dichlorophenyl)-2,3(2,5)-dihydro-3(5)-imino-2-(2-fluoroethyl)-1,2,4-triazine;
5(3)-amino-6-(3,5-dichlorophenyl)-2,3(2,5)-dihydro-3(5)-imino-2-methyl-1,2,4-triazine;
5(3)-amino-6-(3,5-dichlorophenyl)-2,3(2,5)-dihydro-3(5)-imino-2-ethyl-1,2,4-triazine;
5(3)-amino-6-(2,3,5-trichlorophenyl)-2,3(2,5)-dihydro-3(5)-imino-2-(2-fluoroethyl)-1,2,4-triazine;
5(3)-amino-6-(2,3,5-trichlorophenyl)-2,3(2,5)-dihydro-3(5)-imino-2-(3,3,3-trifluoropropyl)-1,2,4-triazine;
5(3)-amino-6-(2,3,dichlorophenyl)-2,3(2,5)-dihydro-3(5)-imino-2-(2,2-difluoroethyl)-1,2,4 triazine.

Another group of compounds of formula (I) includes:
3,5-diamino-6-(2,5-dichlorophenyl)-1,2,4-triazine,
3,5-diamino-6-(3,5-dichlorophenyl)-1,2,4-triazine,
3,5-diamino-6-phenyl-1,2,4-triazine,
3,5-diamino-6-(2,4-dichlorophenyl)-1,2,4-triazine,
3,5-diamino-6-(2-trifluoromethoxyphenyl)-1,2,4-triazine.

Novel compounds of formula (I) include:
5-amino-6-(2,3-dichlorophenyl)-2,3-dihydro-3-imino-2-(2'-fluorophenyl-methyl)-1,2,4-triazine;
5-amino-6-(2,3-dichlorophenyl)-2,3-dihydro-3-imino-2-(3'-fluorophenyl-methyl)-1,2,4-triazine;
5-amino-6-(2,3-dichlorophenyl)-2,3-dihydro-3-imino-2-(4'-fluorophenyl-methyl)-1,2,4-triazine;
5-amino-6-(2,3-dichlorophenyl)-2,3-dihydro-3-imino-2-(2',3'-difluorophenyl-methyl)-1,2,4-triazine;
5-amino-6-(2,3-dichlorophenyl)-2,3-dihydro-3-imino-2-(3'-chlorophenyl-methyl)-1,2,4-triazine;
5-amino-6-(2,3-dichlorophenyl)-2,3-dihydro-3-imino-2-(4'-chlorophenyl-methyl)-1,2,4-triazine;
5-amino-6-(2,3-dichlorophenyl)-2,3-dihydro-3-imino-2-(4'-methylphenyl-methyl)-1,2,4-triazine;
5-amino-6-(2,3-dichlorophenyl)-2,3-dihydro-3-imino-2-(2'-methoxyphenyl-methyl)-1,2,4-triazine;
5-amino-6-(2,3-dichlorophenyl)-2,3-dihydro-3-imino-2-(3'-methoxyphenyl-methyl)-1,2,4-triazine;
5-amino-6-(2,3-dichlorophenyl)-2,3-dihydro-3-imino-2-(4'-methoxyphenyl-methyl)-1,2,4-triazine;
5-amino-6-(2,3-dichlorophenyl)-2,3-dihydro-3-imino-2-(2'-chlorophenyl-methyl)-1,2,4-triazine;
5-amino-6-(2,3-dichlorophenyl)-2,3-dihydro-3-imino-2-(2'-trifluoromethylphenyl-methyl)-1,2,4-triazine;
5-amino-6-(2,3-dichlorophenyl)-2,3-dihydro-3-imino-2-(3'-trifluoromethylphenyl-methyl)-1,2,4-triazine;
5-amino-6-(2,3-dichlorophenyl)-2,3-dihydro-3-imino-2-(4'-trifluoromethylphenyl-methyl)-1,2,4-triazine;
5-amino-6-(2,3-dichlorophenyl)-2,3-dihydro-3-imino-2-(2'-fluoro-3'-trifluoromethylphenyl-methyl)-1,2,4-triazine;
5-amino-6-(2,3-dichlorophenyl)-2,3-dihydro-3-imino-2-(3-thienyl-methyl)-1,2,4-triazine;
5-amino-6-(2,3-dichlorophenyl)-2,3-dihydro-3-imino-2-(3-furyl-methyl)-1,2,4-triazine and
5-amino-6-(2,3-dichlorophenyl)-2,3-dihydro-3-imino-2-(N-boc-piperidin-4-yl-methyl)-1,2,4-triazine;
5-amino-6-(2,3-dichlorophenyl)-2,3-dihydro-3-imino-2-(piperidin-4-yl-methyl)-1,2,4-triazine.

The use of salts of the compounds of formula (I) form an aspect of this invention. Preferred salts are pharmaceutically acceptable acid addition. Suitable pharmaceutically acceptable acid addition salts include those formed with both organic and inorganic acids, for example from hydrochloric, sulphuric, citric, tartaric, phosphoric, lactic, pyruvic, acetic, malonic, succinic, oxalic, fumaric, maleic, oxaloacetic, methanesulphonic, p-toluenesulphonic, benzene-sulphonic, glutamic, naphthoic, and isethionic acids. Esylate (ethanesulfonate), edisylate (1,2-ethanesulfonate), malate, mandalate, benzoate, and salicylate salts are also suitable.

In preparation of the compounds of formula (I), the compound or its salt may be obtained as a solvate of the reaction or crystallisation solvent or a component thereof. Use of such solvates forms another aspect of this invention. Suitable pharmaceutically acceptable solvates include hydrates.

The present invention includes within its scope use of all tautomers, enantiomers and polymorphs of the compounds of formula (I), and of salts and solvates thereof.

The compounds of formula (I) may suitably be prepared by the procedures disclosed in the above-mentioned U.S. Pat. No. 4,649,139, the entire disclosure of which is incorporated herein by reference.

Conveniently, a compound of Formula II

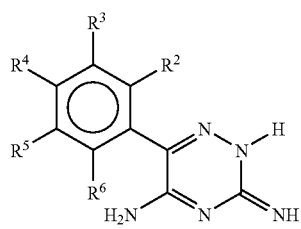

(II)

in which $R^2$-$R^6$ are as defined for formula (I) is reacted with a compound

(III)

where R1 is as defined for formula (I) and Q is a leaving group.

Suitable leaving groups include halogens and sulphonic acid derivatives, such as mesyl, tosyl, etc.

The reaction suitably take places under conventional conditions in a solvent in which the compound of formula II is soluble at a convenient temperature (for example between 0 and 100° C. and most conveniently at room temperature).

Compounds of formula II may be prepared by methods disclosed in EP 0 021 121 A, the entire disclosure of which is incorporated herein by reference.

Salts of compounds of formula (I) may be obtained by the presence of a residual Q acid. Alternatively salts may be prepared by mixing the compound of formula (I) as the free base with a pharmaceutically acceptable acid in a suitable solvent, and removing the solvent to recover the salt, or crystallising the salt from the solvent.

In a further aspect, the present invention provides pharmaceutical compositions for the treatment of disorders such as epilepsy, multiple sclerosis, glaucoma and uevitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria; comprising a compound of formula (I), or a pharmaceutically acceptable salt or solvate thereof, in admixture with a pharmaceutically acceptable carrier.

The compounds of formula (I) will be present in the compositions of the present invention in an effective unit dosage form, that is to say in an amount sufficient to be effective against the disorders in vivo.

The pharmaceutically acceptable carriers present in the compositions of the present invention may be materials conventionally used for the purpose of administering the medicament. These may be liquid or solid materials, which are otherwise inert or medically acceptable and are compatible with the active ingredients.

These pharmaceutical compositions may be given orally or parenterally, for example as a suppository, ointment, cream, powder or trans-dermal patch. However, oral administration and intravenous injection of the compositions are preferred.

For oral administration, fine powders or granules will contain diluting, dispersing and/or surface active agents, and may be presented in draught, in water or in a syrup, in capsules or sachets in the dry state or in non-aqueous suspension wherein suspending agents may be included, or in a suspension in water or syrup. Where desirable or necessary, flavouring, preserving, suspending, or thickening agents can be included. Dry powders or granules may be compressed to form a tablet or contained in a capsule.

For injection, the compounds may be presented in sterile aqueous injection solutions which may contain anti-oxidants or buffers.

The free base or a salt or solvate thereof may also be administered in its pure form unassociated with other additives in which case a capsule or sachet is the preferred carrier.

Alternatively the active compound may be presented in a pure form as an effective unit dosage, for instance compressed as a tablet or the like.

Other compounds which may be included are, for example, medically inert ingredients, e.g., solid and liquid diluents such as lactose, starch, or calcium phosphate for tablet or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Tablets or other forms of presentation provided in discrete units may conveniently contain an amount of compound of formula I which is effective at such dosage or as a multiple of the same, for instance units containing 5 mg to 500 mg, usually around 10 mg to 250 mg.

The pharmaceutical compositions of the present invention may be prepared by the admixture of a compound of formula (I) with a pharmaceutically acceptable carrier. Conventional pharmaceutical excipients may be admixed as required. Example of suitable formulations are give in the above-mentioned U.S. Pat. No. 4,649,139.

The present invention provides a method of treatment of disorders in mammals that are susceptible to sodium channel blockers and antifolates, and particularly disorders such epilepsy, multiple sclerosis, glaucoma and uevitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria; by the administration of a non-toxic effective amount of a compound of formula (I) or a pharmaceutically acceptable salt or solvate thereof, or a composition as hereinbefore defined.

As indicated above, the compounds of formula (I) are generally useful in treating such disorders by oral administration or intravenous injection.

The compounds of formula (I) are normally administered at a dose of from 0.01 mg/kg to 20 mg/kg per day, preferably 0.1 to 5.0 mg/kg per day. The dose range for adult humans is thus generally from 0.7 mg to 1400 mg/day and preferably 7 to 350 mg/day.

In view of the known use in humans of structurally similar compounds such as lamotrigine, no major toxicity problems are anticipated in use of compounds of formula (I). However appropriate testing procedures should be carried out before clinical use.

The following Examples show the preparation of illustrative compounds of formula (I) and other compounds used in testing, as reported below.

EXAMPLE 1

Lamotrigine

Lamotrigine—5(3)-amino-6-(2,3-dichlorophenyl)-2,3(2,5)-dihydro-3(5)-imino-1,2,4-triazine—is approved for human use as an anticonvulsant for treatment of epilepsy and is commercially available under the name LAMICTAL (GSK). The preparation of lamotrigine is disclosed in European Patent No. 0021121.

EXAMPLE 2

5-amino-6-(2,3-dichlorophenyl)-2,3-dihydro-3-imino-2-methyl-1,2,4-triazine

The preparation of the title compound free base is described in U.S. Pat. No. 4,649,139 (Example 1), by reaction of 3,5-diamino-6-(2,3-dichlorophenyl)-1,2,4-triazine with iodomethane. The methanesulfonate salt was prepared from the free base as follows.

Methyl methanesulfonate (0.50 g, 4.5 mmol), 3,5-diamino-6-(2,3-dichlorophenyl)-1,2,4-triazine (0.50 g, 2.0 mmol) and dimethylformamide (4 ml) were stirred and heated at 100° C. for 10 min. The solution was cooled, toluene (20 ml) added, and the mixture stirred for 0.5 h. The solid was collected by filtration and recrystallised from propan-2-ol to give the methanesulfonate salt of the title compound as a white solid (0.40 g), mp 274-276° C.

EXAMPLE 3

5(3)-Amino-6-(2,3-dichlorophenyl)-2,3(2,5)-dihydro-3(5)-imino-2-ethyl-1,2,4-triazine Iodoethane (3.12 g, 0.02 mol) was added to a stirred suspension of 3,5-diamino-6-(2,3-dichlorophenyl)-1,2,4-triazine (2.56 g, 0.01 mol) in acetone (200 ml). The mixture was stirred at room temperature for 5 days, more ethyl iodide added (1.56 g, 0.01 mol) and stirring continued for a further 3 days. The solid was collected by filtration and then stirred in 40 ml of 18% ammonia solution. The solid (ca. 2.5 g) was removed by filtration, dried in vacuo and recrystallised from methanol to give 1.4 g (22%) of the title compound as a white crystalline solid, mp 216-217° C.

$\delta_H$ (500 MHz, dmso-$d_6$) 1.21 (3H, t, J=7.0 Hz, C—$CH_3$), 3.90 (2H, q, J=7.0 Hz, $NCH_2$), 4.15 (1H, brpeak, NH), 6.2-7.2 (2H, vbrpeak, $NH_2$), 7.41 (2H, m, aromatic H), 7.71 (1H, dd, J=8.2 Hz, aromatic H).

Methanesulfonate salt mp 255-260° C.

EXAMPLE 4

5(3)-Amino-6-(2,3-dichlorophenyl)-2,3(2,5)-dihydro-3(5)-imino-2-isopropyl-1,2,4-triazine 2-Iodopropane (2 ml, 3.4 g, 0.02 mol) was added to a stirred suspension of 3,5-diamino-6-(2,3-dichlorophenyl)-1,2,4-triazine (2.56 g, 0.01 mol) in acetone (200 ml). The mixture was stirred at reflux for 5 days, more 2-iodopropane (1 ml, 0.01 mol) added and refluxing continued for 2 days. After cooling, the solid was collected by filtration and then stirred with 0.88 aqueous ammonia (80 ml) for 0.5 h. The solid (ca. 2.5 g) was removed by filtration, dried in vacuo and recrystallised from methanol to give 1.0 g (34%) of the title compound as a pale yellow crystalline solid, mp 209-212° C.

$\delta_H$ (500 MHz, dmso-$d_6$) 1.21 (6H, t, J=7 Hz, $CH_3$—C—$CH_3$), 3.21 (3H, s, $CH_3OH$), 4.15 (1H, brpeak, NH), 4.84 (1H, brpeak, CHN), 7.38-7.46 (2H, m, aromatic H), 7.71 (1H, dd, J=8.2 Hz, aromatic H). This compound is a methanol solvate. Methanesulfonate salt mp 247-250° C.

EXAMPLE 5

5(3)-Amino-6-(2,3-dichlorophenyl)-2,3(2,5)-dihydro-3(5)-imino-2-(2-hydroxyethyl)-1,2,4-triazine 2-Iodoethanol (3.44 g, 0.02 mol) was added to a stirred suspension of 3,5-diamino-6-(2,3-dichlorophenyl)-1,2,4-triazine (2.56 g, 0.01 mol) in acetone (200 ml). The mixture was stirred at reflux for 6 days, cooled and the solid collected by filtration. The solid was stirred with 0.88 aqueous ammonia (100 ml) and the mixture stirred for 0.5 h. The solid (ca. 2.7 g) was removed by filtration, dried in vacuo and recrystallised from methanol to give 1.14 g (38%) of the title compound as a white crystalline solid, mp 217-218° C.

$\delta_H$ (500 MHz, dmso-$d_6$) 3.34 (3H, s, $CH_3OH$), 3.68 (2H, brt, J=6 Hz, $OCH_2$), 3.96 (2H, m, $NCH_2$), 5.5-7.0 (2H, vbrpeak, $NH_2$), 7.36-7.46 (2H, m, aromatic H), 7.71 (1H, dd, J=8.2 Hz, aromatic H). This compound is a methanol solvate Methanesulfonate salt mp 242-245° C.]

EXAMPLE 6

5(3)-Amino-6-(2,3-dichlorophenyl)-2,3(2,5)-dihydro-3(5)-imino-2-propyl-1,2,4-triazine 1-Iodopropane (3.4 g, 0.02 mol) was added to a stirred suspension of 3,5-diamino-6-(2,3-dichlorophenyl)-1,2,4-triazine (2.56 g, 0.01 mol) in acetone (200 ml). The mixture was stirred at reflux for 2 days, more 1-iodopropane (1.7 g, 0.01 mol) added and refluxing continued for a further 24 h. After cooling, the solid was collected by filtration and then stirred with 0.88 aqueous ammonia (80 ml) for 0.5 h. The solid (ca. 3.1 g) was removed by filtration, dried in vacuo and recrystallised from methanol-water (ca. 160 ml) to give 1.65 g (56%) of the title compound as a white crystalline solid, mp 197-199° C.

$\delta_H$ (500 MHz, dmso-$d_6$) 0.88 and 0.91 (3H, 2×t, J=7 Hz, C—$CH_3$), 1.64-1.74 (2H, m, C—$CH_2$—C), 3.82 and 3.90 (2H, 2×t, J=7 Hz, $NCH_2$), 6.2-7.4 (1H, vbrpeak, NH), 7.35-7.46 (2H, m, aromatic H), 7.71 (1H, m, aromatic H). Two tautomers are present in ratio 4:1.

Methanesulfonate salt mp 237-240° C.

EXAMPLE 7

5(3)-Amino-6-(2,3-dichlorophenyl)-2,3(2,5)-dihydro-3(5)-imino-2-isobutyl-1,2,4-triazine methanesulfonate 2-Iodobutane (1.8 ml, 2.88 g, 0.016 mol) was added to a stirred suspension of 3,5-diamino-6-(2,3-dichlorophenyl)-1,2,4-triazine (1.28 g, 0.005 mol) in acetone (50 ml). The mixture was stirred and heated at reflux for 4 days. More 1-iodobutane (0.6 ml, 0.005 mol) was added and refluxing continued for 1 day. After cooling, the solid was collected by filtration and then stirred with 0.88 aqueous ammonia (80 ml) for 0.5 h. The resulting solid (ca.0.9 g) was removed by filtration, dried in vacuo. A portion (0.31 g) was stirred with methanesulfonic acid (0.10 g) in methanol (3.5 ml) and the mixture diluted with ether to give the mesylate of the title compound (0.22 g) as a white crystalline solid, of no sharp mp (decomp.>230° C.

$\delta_H$ (500 MHz, dmso-$d_6$) 0.92 (6H, d, J=5.9 Hz, 2×C—CH$_3$), 2.12 (1H, m, CHMe$_2$), 2.30 (3H, s, SCH$_3$), 3.92 (2H, brs, NCH$_2$), 7.54 (2H, m, aromatic H), 7.86 (1H, dd, J=7.2, 2.5 Hz, aromatic H), 8.18 (1H, brs, NH, exchang.), 8.2-8.8 (2H, vbrpeak, NH$_2$, exchange), 9.14 (1H, brs, NH, exchange.).

EXAMPLE 8

5(3)-Amino-6-(2,3-dichlorophenyl)-2,3(2,5)-dihydro-3(5)-imino-2-butyl-1,2,4-triazine 1-Iodobutane (2.3 ml, 3.68 g, 0.02 mol) was added to a stirred suspension of 3,5-diamino-6-(2,3-dichlorophenyl)-1,2,4-triazine (2.56 g, 0.01 mol) in acetone (200 ml). The mixture was stirred and heated at reflux for 4 days. More 1-iodobutane (0.6 ml, 0.005 mol) was added and refluxing continued for 1 day. After cooling, the solid was collected by filtration and then stirred with 0.88 aqueous ammonia (80 ml) for 0.5 h. The resulting solid (ca.2.2 g) was removed by filtration, dried in vacuo and recrystallised from methanol to give 1.1 g (35%) of the title compound as a white crystalline solid, mp 175° C.

$\delta_H$ (500 MHz, dmso-$d_6$) 0.89 (3H, t, J=7 Hz, CH$_3$), 1.31 (2H, hextet, J=7 Hz, CH$_2$Me), 1.64 (2H, pent, J=7 Hz, CH$_2$—C-Me), 3.86 (2H, t, J=7 Hz, NCH$_2$), 6.2-7.2 (2H, vbrpeak, NH$_2$) 7.38 (1H, dd, J=8.2 Hz, aromatic H), 7.43 (1H, t, J=8 Hz, aromatic H), 7.70 (1H, dd, J=8.2 Hz, aromatic H).

EXAMPLE 9

5(3)-Amino-6-(2,3-dichlorophenyl)-2,3(2,5)-dihydro-3(5)-imino-2-phenylmethyl-1,2,4-triazine hemimethanesulfonate Benzyl chloride (0.92 ml, 1.01 g, 0.008 mol) was added to a stirred suspension of 3,5-diamino-6-(2,3-dichlorophenyl)-1,2,4-triazine (1.0 g, 0.004 mol) in acetone (50 ml). The mixture was stirred and heated at reflux for 3 days. More benzyl chloride (0.6 ml, 0.005 mol) was added and refluxing continued for 2 days. After cooling, the solid was collected by filtration and then stirred with 0.88 aqueous ammonia (80 ml) for 0.5 h. The resulting solid (ca.0.64 g) was removed by filtration, dried in vacuo. A portion (0.35 g) was stirred with methanesulfonic acid (0.10 g) in methanol (3.5 ml) and the mixture diluted with ether to give the mesylate of the title compound (0.14 g) as a white crystalline solid, of no sharp mp (decomp.>270° C.

$\delta_H$ (500 MHz, dmso-$d_6$) 2.31 (1.5H, s, SCH$_3$), 5.42 (2H, brs, NCH$_2$), 7.39 (5H, m, aromatic H), 7.56 (2H, m, aromatic H), 7.86 (1H, dd, J=7.2, 2.4 Hz, aromatic H), 8.28 (1H, s, NH, exchang.), 8.4-8.8 (2H, vbrpeak, NH$_2$, exchang.), 9.28 (1H, s, NH, exchang.).

The spectrum indicates stoichiometry of heterocycle.0.5 MeSO$_3$H m/z 347 (M$^+$+1).

EXAMPLE 10

5(3)-Amino-6-(2,3-dichlorophenyl)-2,3(2,5)-dihydro-3(5)-imino-2-(prop-2-enyl)-1,2,4-triazine hemimethanesulfonate Allyl bromide (1.8 ml, 2.52 g, 0.02 mol) was added to a stirred suspension of 3,5-diamino-6-(2,3-dichlorophenyl)-1,2,4-triazine (1.28 g, 0.005 mol) in acetone (50 ml). The mixture was stirred and heated at reflux for 4 days. More allyl bromide (0.6 ml, 0.007 mol) was added and refluxing continued for 1 day. After cooling, the solid was collected by filtration and then stirred with 0.88 aqueous ammonia (80 ml) for 0.5 h. The resulting solid (ca.0.84 g) was removed by filtration, dried in vacuo. A portion (0.30 g) was stirred with methanesulfonic acid (0.10 g) in methanol (3.5 ml) and the mixture diluted with ether to give the mesylate of the title compound (0.26 g) as a fawn crystalline solid, of no sharp mp (decomp.>270° C.

$\delta_H$ (500 MHz, dmso-$d_6$) 2.31 (1.5H, s, SCH$_3$), 4.74 (2H, d, J=4.8 Hz, NCH$_2$), 5.28 (2H, m, olefinic H), 5.93 (1H, m, olefinic H), 7.54 (2H, m, aromatic H), 7.86 (1H, m, aromatic H), 8.20 (1H, s, NH, exchang.), 8.2-8.8 (2H, vbrpeak, NH$_2$, exchang.), 9.2 (1H, s, NH, exchang.).

The spectrum indicates stoichiometry of heterocycle.0.5 MeSO$_3$H.

EXAMPLE 11

5(3)-Amino-6-(2,3-dichlorophenyl)-2,3(2,5)-dihydro-3(5)-imino-1,2,4-triazin-2-yl]acetamide 2-(carboxamido)methyllamotrigine)

2-Iodoacetamide (1.85 g, 0.01 mol) was added to a stirred suspension of 3,5-diamino-6-(2,3-dichlorophenyl)-1,2,4-triazine (1.28 g, 0.005 mol) in acetone (50 ml). The mixture was stirred and heated at reflux for 4 h. After cooling, the solid was collected by filtration and then stirred with 0.88 aqueous ammonia (50 ml) for 0.5 h. The resulting solid (ca.1.1 g) was removed by filtration, dried in vacuo and recrystallised from acetonitrile to give 0.56 g (36%) of the title compound as a white crystalline solid of no sharp mp (decomp. above 270° C.).

$\delta_H$ (500 MHz, dmso-$d_6$) 2.07 (CH$_3$CN), 4.44 (2H, brs, NCH$_2$), 6.0-7.0 (2H, vbrpeak, NH$_2$), 7.13 (1H, brs, NH, exchang.), 7.37 (1H, dd, J=8.2 Hz, aromatic H), 7.44 (1H, t, J=8 Hz, aromatic H), 7.49 (1H, brs, NH, exchang.), 7.71 (1H, dd, J=8.2 Hz, aromatic H).

m/z 313 (M$^+$).

EXAMPLE 12

5(3)-Amino-6-(2,3-dichlorophenyl)-2,3(2,5)-dihydro-3(5)-imino-2-(4-methyl)phenylmethyl-1,2,4-triazine 4-Methylbenzyl bromide (0.70 g, 4.3 mmol) was added to a stirred suspension of 3,5-diamino-6-(2,3-dichlorophenyl)-1,2,4-triazine (0.64 g, 2.5 mmol), NaI (0.1 g) and acetone (25 ml). The mixture was stirred and heated at reflux for 3 h. After cooling, the solid was collected by filtration and then stirred with 0.88 aqueous ammonia-water (40 ml, 1:1) for 0.5 h. The resulting solid (ca.0.7 g) was removed by filtration and dried in vacuo. Recrystallisation from ethanol gave the product (0.44 g) as a white solid, mp 180-185° C. (decomp.).

$\delta_H$ (500 MHz, dmso-$d_6$) 2.27 (3H, s, CH$_3$), 5.05 (2H, s, NCH$_2$), 7.14 (2H, d, J=8 Hz, aromatic H), 7.22 (2H, d, J=8 Hz, aromatic H), 7.38 (1H, dd, J=7.5, 2 Hz, aromatic H), 7.44 (1H, d, J=7.5 Hz, aromatic H), 7.71 (1H, dd, J=7.5, 2 Hz). The spectrum indicates that the compound contains 0.3EtOH. m/z 361 (M$^+$+1).

EXAMPLE 13

5(3)-Amino-6-(2,3-dichlorophenyl)-2,3(2,5)-dihydro-3(5)-imino-2-(2,3-difluoro)phenylmethyl-1,2,4-triazine 2,3-Difluorobenzyl bromide (2.07 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 6 h. After cooling, the solid was collected by filtration and then stirred with 0.88 aqueous ammonia-water (80 ml, 1:1) for 0.5 h. The resulting solid (ca.2 g) was removed by filtration and dried in vacuo. Recrystallisation from methanol gave the product (1.2 g) as a pale yellow solid, mp 208-209° C.

$\delta_H$ (500 MHz, dmso-$d_6$) 5.20 (2H, s, NCH$_2$), 5.66 (1H, brpeak, NH), 6.63 (1H, brpeak, NH), 7.19 (2H, m, aromatic H), 7.35 (1H, m, aromatic H), 7.44 (2H, m, aromatic H), 7.72 (1H, brd, J=7 Hz, aromatic H).

m/z 383 (M$^+$+1).

EXAMPLE 14

5(3)-Amino-6-(2,3-dichlorophenyl)-2,3(2,5)-dihydro-3(5)-imino-2-(2-fluoro)phenylmethyl-1,2,4-triazine 2-Fluorobenzyl chloride (1.45 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.2 g) was removed by filtration and dried in vacuo. Recrystallisation from methanol gave the product (1.2 g) as a pale yellow solid, mp 201-203° C.

$\delta_H$ (500 MHz, dmso-$d_6$) 5.16 (2H, s, NCH$_2$), 6-7 (2H, vbr peak, NH$_2$), 7.18 (2H, m, aromatic H), 7.33 (2H, m, aromatic H), 7.42 (2H, m, aromatic H), 7.72 (1H, dd, J=7.5, 1.5 Hz). The spectrum indicated the compound contained 0.5MeOH.

m/z 365 (M$^+$+1).

EXAMPLE 15

5(3)-Amino-6-(2,3-dichlorophenyl)-2,3(2,5)-dihydro-3(5)-imino-2-(3-fluoro)phenylmethyl-1,2,4-triazine 3-Fluorobenzyl chloride (1.45 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.1.5 g) was removed by filtration and dried in vacuo. Recrystallisation from methanol gave the product (0.42 g) as a pale yellow solid, mp 189-190° C.

$\delta_H$ (500 MHz, dmso-$d_6$) 5.13 (2H, s, NCH$_2$), 6-7 (2H, vbr peak, NH$_2$), 7.14 (3H, m, aromatic H), 7.43 (3H, m, aromatic H), 7.72 (1H, dd, J=7.5, 1.5 Hz).

m/z 365 (M$^+$+1).

EXAMPLE 16

5(3)-Amino-6-(2,3-dichlorophenyl)-2,3(2,5)-dihydro-3(5)-imino-2-(4-fluoro)phenylmethyl-1,2,4-triazine 4-Fluorobenzyl chloride (1.45 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.1.6 g) was removed by filtration and dried in vacuo. Recrystallisation from methanol gave the product (1.1 g) as a pale yellow solid, mp 189-190° C.

$\delta_H$ (500 MHz, dmso-$d_6$) 5.08 (2H, s, NCH$_2$), 6-7 (2H, vbr peak, NH$_2$), 7.17 (2H, t, J=8 Hz, aromatic H), 7.40 (4H, m, aromatic H), 7.71 (1H, dd, J=7, 2 Hz, aromatic H). m/z 365 (M$^+$+1).

EXAMPLE 17

5(3)-Amino-6-(2,3-dichlorophenyl)-2,3(2,5)-dihydro-3(5)-imino-2-(2-methoxy)phenylmethyl-1,2,4-triazine 2-Methoxybenzyl chloride (1.56 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.1.8 g) was removed by filtration and dried in vacuo. Recrystallisation from ethanol gave the product (0.95 g) as a pale yellow solid, mp 194-196° C.

$\delta_H$ (500 MHz, dmso-$d_6$) 3.80 (3H, s, OCH$_3$), 5.05 (2H, brs, NCH$_2$), 6.5-7.0 (1H, vbrpeak, NH), 6.92 (1H, t, J=8 Hz, aromatic H), 7.01 (2H, brt, J=8 Hz, aromatic H), 7.26 (1H, brt, J=8 Hz, aromatic H), 7.40 (2H, m, aromatic H), 7.69 (1H, brd, J=8 Hz, aromatic H).

m/z 377 (M$^+$+1).

EXAMPLE 18

5(3)-Amino-6-(2,3-dichlorophenyl)-2,3(2,5)-dihydro-3(5)-imino-2-(3-methoxy)phenylmethyl-1,2,4-triazine 3-Methoxybenzyl chloride (1.56 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.1.4 g) was removed by filtration and dried in vacuo. Recrystallisation from ethanol gave the product (0.64 g) as a pale yellow solid, mp 192-195° C.

$\delta_H$ (500 MHz, dmso-$d_6$) 3.73 (3H, s, OCH$_3$), 5.07 (2H, brs, NCH$_2$), 6.5-7.0 (1H, vbrpeak, NH), 6.84 (1H, brd, J=8 Hz, aromatic H), 6.88 (2H, m, aromatic H), 7.26 (1H, t, J=8 Hz, aromatic H), 7.42 (2H, m, aromatic H), 7.71 (1H, d, J=7 Hz, aromatic H).

m/z 377 (M$^+$+1).

EXAMPLE 19

5(3)-Amino-6-(2,3-dichlorophenyl)-2,3(2,5)-dihydro-3(5)-imino-2-(4-methoxy)phenylmethyl-1,2,4-triazine 4-Methoxybenzyl chloride (1.56 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.1.6 g) was removed by filtration and dried in vacuo. Recrystallisation from ethanol gave the product (0.83 g) as a pale yellow solid, mp 212-215° C.

m/z 377 (M$^+$+1).

EXAMPLE 20

5(3)-Amino-6-(2,3-dichlorophenyl)-2,3(2,5)-dihydro-3(5)-imino-2-(3-chloro)phenylmethyl-1,2,4-triazine 3-Chlorobenzyl bromide (2.05 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.1.2 g) was removed by filtration and dried in vacuo. Recrystallisation from methanol gave the product (0.35 g) as a pale yellow solid, mp 178-180° C.

$\delta_H$ (500 MHz, dmso-d$_6$) 5.11 (2H, brs, NCH$_2$), 6.5-7.0 (1H, vbrpeak, NH), 7.28 (1H, brd, J=8 Hz, aromatic H), 7.32-7.47 (5H, m, aromatic H), 7.72 (1H, dd, J=7, 2 Hz, aromatic H). The spectrum indicates the presence of 0.75MeOH.

m/z 381,383 (M$^+$+1).

EXAMPLE 21

5(3)-Amino-6-(2,3-dichlorophenyl)-2,3(2,5)-dihydro-3(5)-imino-2-(4-chloro)phenylmethyl-1,2,4-triazine 4-Chlorobenzyl chloride (1.61 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.1.5 g) was removed by filtration and dried in vacuo. Recrystallisation from methanol gave the product (0.71 g) as a pale yellow solid, mp 192-193° C.

$\delta_H$ (500 MHz, dmso-d$_6$) 5.09 (2H, s, NCH$_2$), 5.5 (1H, vbrpeak, NH), 6.5 (1H, vbrpeak, NH), 7.35 (2H, d, J=8 Hz, aromatic H), 7.42 (4H, m, aromatic H), 7.72 (1H, brd, J=7 Hz, aromatic H).

m/z 381,383 (M$^+$+1).

EXAMPLE 22

5(3)-Amino-6-(2,3-dichlorophenyl)-2,3(2,5)-dihydro-3(5)-imino-2-(2-chloro)phenylmethyl-1,2,4-triazine 2-Chlorobenzyl bromide (2.06 g, 10 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.1.5 g) was removed by filtration and dried in vacuo. Recrystallisation from methanol gave the product (0.71 g) as a pale yellow solid, mp 205° C. (decomp.).

$\delta_H$ (500 MHz, dmso-d$_6$) 3.32 (3H, s, MeOH), 5.18 (2H, s, NCH$_2$), 5.6 (1H, brpeak, NH, exchang.), 6.6 (1H, brpeak, NH, exchang.), 7.20 (1H, m, aromatic H), 7.32 (2H, m, aromatic H), 7.46 (3H, m, aromatic H), 7.70 (1H, brd, J=7 Hz, aromatic H).

m/z 381,383 (M$^+$+1).

EXAMPLE 23

5(3)-Amino-6-(2,3-dichlorophenyl)-2,3(2,5)-dihydro-3(5)-imino-2-(2-trifluoromethyl)phenylmethyl-1,2,4-triazine 2-trifluoromethylbenzyl bromide (0.56 g, 2.2 mmol) was added to a stirred suspension of 3,5-diamino-6-(2,3-dichlorophenyl)-1,2,4-triazine (0.56 g, 2.2 mmol), NaI (0.1 g) and acetone (25 ml). The mixture was stirred and heated at reflux for 5 h. After cooling, the solid was collected by filtration and then stirred with 0.88 aqueous ammonia-water (40 ml, 1:1) for 0.5 h. The resulting solid (ca.1.5 g) was removed by filtration and dried in vacuo. Recrystallisation from methanol gave the product (0.42 g) as a pale yellow solid, mp 200-201° C.

$\delta_H$ (500 MHz, dmso-d$_6$) 3.32 (3H, s, MeOH), 5.31 (2H, s, NCH$_2$), 5.66 (1H, brs, NH, exchang.), 6.66 (1H, brs, NH, exchang.), 7.31 (1H, d, J=8 Hz, aromatic H), 7.45 (3H, m, aromatic H), 7.5 (1H, br peak, NH, exchang.), 7.72 (3H, m, aromatic H).

m/z 414, 416 (M$^+$+1).

EXAMPLE 24

5(3)-Amino-6-(2,3-dichlorophenyl)-2,3(2,5)-dihydro-3(5)-imino-2-(3-trifluoromethyl)phenylmethyl-1,2,4-triazine 3-Trifluoromethylbenzyl bromide (2.0 g, 8.7 mmol) was added to a stirred suspension of 3,5-diamino-6-(2,3-dichlorophenyl)-1,2,4-triazine (1.12 g, 4.4 mmol), NaI (0.1 g) and acetone (50 ml). The mixture was stirred and heated at reflux for 5 h. After cooling, the solid was collected by filtration and then stirred with 0.88 aqueous ammonia-water (80 ml, 1:1) for 0.5 h. The resulting solid (ca.1.2 g) was removed by filtration and dried in vacuo. Recrystallisation from methanol gave the product (0.52 g) as a pale yellow solid, mp 168-170° C.

$\delta_H$ (500 MHz, dmso-d$_6$) 3.32 (3H, s, MeOH), 5.22 (2H, brs, NCH$_2$), 5.4-5.8 (1H, vbrpeak, NH, exchang.), 6.4-6.8 (1H, brs, NH, exchang.), 7.42 (2H, m, aromatic H), 7.63 (4H, m, aromatic H), 7.73 (1H, brd, J=7 Hz, aromatic H). m/z 414, 416 (M$^+$+1).

EXAMPLE 25

5(3)-Amino-6-(2,3-dichlorophenyl)-2,3(2,5)-dihydro-3(5)-imino-2-(4-trifluoromethyl)phenylmethyl-1,2,4-triazine 4-Trifluoromethylbenzyl chloride (1.0 g, 4.0 mmol) was added to a stirred suspension of 3,5-diamino-6-(2,3-dichlorophenyl)-1,2,4-triazine (0.56 g, 2.2 mmol), NaI (0.1 g) and acetone (25 ml). The mixture was stirred and heated at reflux for 5 h. After cooling, the solid was collected by filtration and then stirred with 0.88 aqueous ammonia-water (40 ml, 1:1) for 0.5 h. The resulting solid (ca.0.7 g) was removed by filtration and dried in vacuo. Recrystallisation from methanol gave the product (0.42 g) as a pale yellow solid, mp 198-200° C.

$\delta_H$ (500 MHz, dmso-d$_6$) 3.32 (3H, s, MeOH), 5.20 (2H, brs, NCH$_2$), 5.3-5.8 (1H, vbrpeak, NH, exchang.), 6.4-6.8 (1H, brs, NH, exchang.), 7-8 (1H, vbrpeak, NH, exchang.), 7.43 (2H, m, aromatic H), 7.53 (2H, brd, J=8 Hz, aromatic H), 7.73 (3H, brd, J=8 Hz, aromatic H). m/z 414, 416 (M$^+$+1).

EXAMPLE 26

5(3)-Amino-6-(2,3-dichlorophenyl)-2,3(2,5)-dihydro-3(5)-imino-2-(2-fluoro-3-trifluoromethyl)phenylmethyl-1,2,4-triazine 2-Fluoro-3-trifluoromethylbenzyl bromide (1.0 g, 4.0 mmol) was added to a stirred suspension of 3,5-diamino-6-(2,3-dichlorophenyl)-1,2,4-triazine (0.56 g, 2.2 mmol), NaI (50 mg) and acetone (25 ml). The mixture was stirred and heated at reflux for 5 h. After cooling, the solid was collected by filtration and then stirred with 0.88 aqueous ammonia-water (40 ml, 1:1) for 0.5 h. The resulting solid (ca.0.7 g) was removed by filtration and dried in vacuo. Recrystallisation from methanol gave the product (0.40 g) as a pale yellow solid, mp>250° C. (decomp.).

$\delta_H$ (500 MHz, dmso-d$_6$) 3.32 (3H, s, MeOH), 5.23 (2H, brs, NCH$_2$), 5.67 (1H, brs, NH, exchang.), 6.5-7.0 (1H, vbrpeak, NH, exchang.), 7.42 (3H, m, aromatic H), 7.5 (1H, brpeak, NH, exchang.), 7.70 (3H, m, aromatic H).
m/z 432,434(M$^+$+1).

EXAMPLE 27

4-{[5(3)-Amino-6-(2,3-dichlorophenyl)-2,3-dihydro-3(5)-imino-1,2,4-triazin-2-yl]methyl}benzamide or 5(3)-Amino-6-(2,3-dichlorophenyl)-2,3(2,5)-dihydro-3(5)-imino-2-(3-carboxamido)phenylmethyl-1,2,4-triazine 3-(chloromethyl)benzamide was prepared by reaction of 3-chloromethylbenzoyl chloride with ammonia according to the procedure of C. Y. Watson et al, *Bioorg. & Med. Chem.*, 6, 721-734 (1998).

(3-Chloromethyl)benzamide (1.33 g, 7.8 mmol) was added to a stirred suspension of 3,5-diamino-6-(2,3-dichlorophenyl)-1,2,4-triazine (1.61 g, 6.3 mmol), NaI (0.1 g) and acetone (70 ml). The mixture was stirred and heated at reflux overnight. After cooling, the solid was collected by filtration and then stirred with 0.88 aqueous ammonia-water (80 ml, 1:1) for 0.5 h. The resulting solid (ca.1.5 g) was removed by filtration and dried in vacuo. Recrystallisation from methanol gave the product (0.92 g) as a pale yellow solid, mp 228-230° C.

$\delta_H$ (500 MHz, dmso-d$_6$) 3.32 (3H, s, MeOH), 5.15 (2H, brs, NCH$_2$), 5.4-5.8 (1H, vbrpeak, NH, exchang.), 6.4-6.8 (1H, vbrpeak, NH, exchang.), 7.34 (1H, brs, NH, exchang.), 7.38-7.48 (4H, m, aromatic H), 7.70 (1H, brd, J=8 Hz, aromatic H.), 7.76 (1H, brs, J=8 Hz, aromatic H), 7.84 (1H, brs, aromatic H), 7.96 (1H, brs, NH, exchang.). m/z 389, 391 (M$^+$+1).

EXAMPLE 28

4-{[5(3)-Amino-6-(2,3-dichlorophenyl)-2,3-dihydro-3(5)-imino-1,2,4-triazin-2-yl]
methyl}phenylmethanol or 5(3)-Amino-6-(2,3-dichlorophenyl)-2,3(2,5)-dihydro-3(5)-imino-2-(4-hydroxymethyl)phenylmethyl-1,2,4-triazine 4-(Chloromethyl)benzyl alcohol (1.0 g, 6.4 mmol) was added to a stirred suspension of 3,5-diamino-6-(2,3-dichlorophenyl)-1,2,4-triazine (1.28 g, 5 mmol), NaI (0.1 g) and acetone (50 ml). The mixture was stirred and heated at reflux for 10 h. After cooling, the solid was collected by filtration and then stirred with 0.88 aqueous ammonia-water (80 ml, 1:1) for 0.5 h. The resulting solid (ca.1.3 g) was removed by filtration and dried in vacuo. Recrystallisation from methanol gave the product (0.47 g) as a pale yellow solid, mp 215-217° C.

$\delta_H$ (500 MHz, dmso-d$_6$) 3.32 (3H, s, MeOH), 4.47 (2H, d, J=5 Hz, OH, exchang.), 5.08 (2H, brs, NCH$_2$), 5.14 (1H, brt, J=5 Hz, OH, exchang.), 5.4-5.8 (1H, vbrpeak, NH, exchang.), 6.4-6.8 (1H, vbrpeak, NH, exchang.), 7.28 (4H, m, aromatic H), 7.40 (1H, brd, J=8 Hz, aromatic H), 7.45 (1H, t, J=8 Hz, aromatic H), 7.72 (1H, brd, J=8 Hz, aromatic H).
m/z 376, 378 (M$^+$+1).

EXAMPLE 29

5(3)-Amino-6-(2,3-dichlorophenyl)-2,3(2,5)-dihydro-3(5)-imino-2-(3-thienylmethyl)-1,2,4-triazine 3-chloromethylthiophene was prepared by chlorination of thiophene-3-methanol according to the procedure of S. Gronowitz and S. Liljefors, *Chemica Scipta,* 13, 39-45 (1978-79).

2-Chloromethylthiophene (1.04 g, 7.8 mmol) was added to a stirred suspension of 3,5-diamino-6-(2,3-dichlorophenyl)-1,2,4-triazine (1.00 g, 3.9 mmol), NaI (0.07 g) and acetone (35 ml). The mixture was stirred and heated at reflux for 36 h. After cooling, the solid was collected by filtration and then stirred with 0.88 aqueous ammonia-water (30 ml, 1:1) for 5 h. The resulting solid (ca.0.5 g) was removed by filtration and dried in vacuo. Recrystallisation from methanol gave the product (0.22) as a cream solid, mp 191-192° C. (decomp.).

$\delta_H$ (500 MHz, dmso-d$_6$) 3.32 (3H, s, CH$_3$OH), 5.07 (2H, s, NCH$_2$), 5.2-6.0 (1H, vbr peak, NH, exchang.), 6.5-7.5 (2H, vbrpeak, NH$_2$), 7.11 (1H, dd, J=5, 1 Hz, aromatic H), 7.37-7.45 (3H, m, aromatic H), 7.50 (1H, m, aromatic H), 7.72 (1H, dd, J=7.5, 2 Hz). The spectrum indicates that the compound contains 1.0MeOH. m/z 353 (M$^+$+1).

EXAMPLE 30

5(3)-Amino-6-(2,3-dichlorophenyl)-2,3(2,5)-dihydro-3(5)-imino-2-(3-furanylmethyl)-1,2,4-triazine 3-chloromethylfuran was prepared by chlorination of furan-3-methanol according to the procedure of E. Sherman and E. D. Amstutz, *J. Am. Chem. Soc.,* 72, 2195-2199 (1950).

3-Chloromethylfuran (0.90 g, 7.7 mmol) was added to a stirred suspension of 3,5-diamino-6-(2,3-dichlorophenyl)-1,2,4-triazine (1.00 g, 3.9 mmol), NaI (0.07 g) and acetone (40 ml). The mixture was stirred and heated at reflux for 36 h. After cooling, the solid was collected by filtration and then stirred with 0.88 aqueous ammonia-water (30 ml, 1:1) for 5 h. The resulting solid (ca. 1.1 g) was removed by filtration and dried in vacuo. Recrystallisation from methanol gave the product (0.72 g) as a cream solid, mp 191-193° C.

$\delta_H$ (500 MHz, dmso-d$_6$) 3.32 (3H, s, CH$_3$OH), 4.92 (2H, s, NCH$_2$), 5.5-6.4 (1H, vbr peak, NH, exchang.), 6.48 (1H, brs, furan H), 6.5-7.5 (2H, vbrpeak, NH$_2$), 7.37-7.46 (2H, m, aromatic H), 7.61 (1H, brs, furan H), 7.64 (1H, brs, furan H), 7.71 (1H, dd, J=7.5, 2 Hz, aromatic H). The spectrum indicates that the compound contains 1.0MeOH.
m/z 337 (M$^+$+1).

EXAMPLE 31

6-(2,3,5-trichlorophenyl)-1,2,4-triazine-3,5-diamine prepared according to the method described in U.S. Pat. No. 4,602,017; mp 232-235° C.

EXAMPLE 32

5(3)-Amino-6-(2,3,5-trichlorophenyl)-2,3(2,5)-dihydro-3(5)-imino-2-methyl-1,2,4-triazine Iodomethane (0.40 g, 2.8 mmol) was added to a stirred suspension of 3,5-diamino-6-(2,3,5-trichlorophenyl)-1,2,4-triazine (0.20 g, 0.7 mmol) in acetone (15 ml). The mixture was stirred at room temperature for 6 days and the solvent removed in vacuo at 40° C. Ice (ca. 4 g) was added to the residue followed by 0.88 aqueous ammonia (3 ml) and the mixture stirred for 4 h. The solid was removed by filtration, dried in vacuo and recrystallised from ethanol to give 0.13 g of the title compound as an off-white crystalline solid, mp 225-226° C.

$\delta_H$ (500 MHz, dmso-$d_6$) 3.47 (3H, s, NCH$_3$), 5.5-7.4 (3H, vbr peak, NH, exchang.), 7.56 (1H, d, J=2.5 Hz, aromatic H), 7.92 (1H, dd, J=2.5 Hz, aromatic H).

m/z 304-306 (M$^+$+1).

EXAMPLE 33

6-(2,3-difluorophenyl)-1,2,4-triazine-3,5-diamine

Step 1 2,3-Difluorobenzoyl chloride 2,3-Difluorobenzoic acid (11.6 g, 0.07 mol), thionyl chloride (37.5 ml, 61.1 g, 0.5 mol) and toluene (80 ml) were heated at reflux for 3 h. The solution was cooled and the volatiles were removed in vacuo. The residue was azeotroped with toluene (2×30 ml) to give the product (10.8 g) as a clear yellow oil.

Step 2 2,3-Difluorobenzoyl cyanide

Copper(1) cyanide (6.6 g, 0.07 mol), potassium iodide (12.2 g, 0.07 mol) and xylene (70 ml) were heated at reflux for 24 h using a Dean-stark apparatus. A solution of 2,3-difluorobenzoyl chloride (10.8 g, 0.06 mol) in xylene (40 ml) was added. The resulting suspension was refluxed under N$_2$ at 165° C. for 3 days using a Dean-Stark apparatus. After cooling, inorganic salts were removed by filtration and the filtrate concentrated in vacuo. The residue was azeotroped with toluene (2×30 ml) to give the product (7.2 g) as a brown solid.

Step 3 2-(2,3-Difluorophenyl)-2-guanidinoimino) acetonitrile

Conc. sulfuric acid (43.5 ml, 80 g, 0.82 mol) was added slowly to water (45 ml) with stirring. Aminoguanidine bicarbonate (4.4 g, 0.032 mol) was added slowly to this hot acid solution with stirring (caution! CO$_2$ evolved) and stirring was continued for a further 15 min. A solution of 2,3-difluorobenzoyl cyanide (3.1 g, 0.019 mol) in acetonitrile (20 ml) was added dropwise over 0.5 h to the above solution of aminoguanidine sulfate and the mixture was stirred at room temperature for 4 days. Aqueous NaOH solution (4M) was then added carefully, with cooling in an ice-bath, until the mixture was at pH 7. The precipitate was collected by filtration, washed with water and dried to give the product (2.9 g) as a yellow solid, mp 168-170° C.

Step 4

2-(2,3-Difluorophenyl)-2-guanidinoimino)acetonitrile (2.8 g, 0.01 mol) and propan-1-ol (30 ml) were stirred and heated at reflux for 1.5 h. The cool solution was concentrated in vacuo and the residue chromatographed on silica (250 g). Elution with CH$_2$Cl$_2$-MeOH (95:5) gave a tan solid. This material was slurried in CH$_2$Cl$_2$ and the remaining insolubles collected by filtration to give the product (1.3 g) as a cream solid, mp 229-230° C.

$\delta_H$ (500 MHz, dmso-$d_6$) 6.42 (2H, brs, NH$_2$, exchang.), 6.6-7.0 (2H, vbr peak, NH$_2$, exchang.), 7.25 (1H, brt, J=7.5 Hz, aromatic H), 7.30 (1H, m, aromatic H), 7.48 (1H, m, aromatic H). m/z 224 (M$^+$+1).

EXAMPLE 34

5(3)-Amino-6-(2,3,5-trichlorophenyl)-2,3(2,5)-dihydro-3(5)-imino-2-propyl-1,2,4-triazine Iodopropane (0.51 g, 3 mmol) was added to a stirred suspension of 3,5-diamino-6-(2,3,5-trichlorophenyl)-1,2,4-triazine (0.29 g, 1 mmol) in acetone (15 ml). The mixture was stirred and heated at reflux for 8 days. After cooling, the precipitate was collected by filtration, and then stirred in water (4 ml) and aqueous ammonia (2 ml) for 4 h. The solid was removed by filtration, dried in vacuo and recrystallised from methanol to give 0.15 g of the title compound as an off-white crystalline solid, mp 240-243° C.

$\delta_H$ (500 MHz, dmso-$d_6$) 0.88 (3H, t, J=7.5 Hz, CH$_3$), 1.67 (2H, hext, J=7.5 Hz, CH$_2$), 3.82 (2H, t, J=7.5 Hz, NCH$_2$), 6.3-7.3 (2H, vbr peak, NH$_2$, exchang.), 7.56 (1H, d, J=2.5 Hz, aromatic H), 7.92 (1H, d, J=2.5 Hz, aromatic H).

m/z 332-334 (M$^+$+1).

EXAMPLE 35

3-chloro-2-fluorophenyl)-1,2,4-triazine-3,5-diamine

Step 1 3-Chloro-2-fluorobenzoic acid

3-Chloro-2-fluorobenzaldehyde (15.9 g, 0.1 mol) was dissolved in tert-butanol (60 ml), stirred and heated under N$_2$ at 50° C. 2M aqueous NaOH (100 ml, 0.2 mol) was warmed to 50° C. and added to the solution of the aldehyde. Aqueous hydrogen peroxide solution (H$_2$O$_2$, 30%, 70 ml, 0.6 mol) was added over 45 min, maintaining the temperature at 55-60° C. The mixture was stirred and heated under N$_2$ for a further 1 h, cooled and concentrated in vacuo. The residual slurry was filtered. The filtrate was washed with toluene (2×xx ml) and acidified to pH 1 with 5N hydrochloric acid whilst stirring vigorously. The resulting solid was collected by filtration, washed with water and dried in vacuo at 50° C. to give 11.1 g of product, mp 179-181° C.

A sample prepared by a different route [J. Mortier et al, *Tetrahedron Lett.*, 36, 881-884 (1995)] is reported to have mp 179-181° C.

Step 2 3-Chloro-2-fluorobenzoyl chloride

3-Chloro-2-fluorobenzoic acid (10.0 g, 0.06 mol), thionyl chloride (31 ml, 50 g, 0.4 mol) and dry toluene (40 ml) were heated at reflux for 3 h. The solution was cooled and the volatiles were removed in vacuo. The residue was azeotroped with toluene (2×30 ml) to give the product (11.5 g) as a clear yellow oil.

Step 3 3-Chloro-2-\fluorobenzoyl cyanide

Copper(1) cyanide (6.6 g, 0.07 mol), potassium iodide (12.2 g, 0.07 mol) and xylene (50 ml) were heated at reflux for 24 h using a Dean-stark apparatus. A solution of 3-chloro-2-fluorobenzoyl chloride (11.5 g, 0.06 mol) in xylene (15 ml) was added. The resulting suspension was refluxed under $N_2$ at 165° C. for 3 days using a Dean-Stark apparatus. After cooling, inorganic salts were removed by filtration and the filtrate concentrated in vacuo. The residue was azeotroped with toluene (2×30 ml) to give the product (9.5 g) as a brown solid.

Step 4 2-(3-Chloro-2-fluorophenyl)-2-guanidinoimino)acetonitrile

Conc. sulfuric acid (43.5 ml, 150 g, 1.6 mol) was added slowly to water (45 ml) with stirring. Aminoguanidine bicarbonate (5.7 g, 0.036 mol) was added slowly to this hot acid solution with stirring (caution! $CO_2$ evolved) and stirring was continued for a further 15 min. A solution of 3-chloro-2-fluoro-benzoyl cyanide (4.3 g, 0.02 mol) in acetonitrile (31 ml) was added dropwise over 0.5 h to the above solution of aminoguanidine sulfate and the mixture was stirred at room temperature for 4 days. Aqueous NaOH solution (4M) was then added carefully, with cooling in an ice-bath, until the mixture was at pH 7. The precipitate was collected by filtration, washed with water and dried to give the product (3.2 g) as a tan solid.

Step 5

2-(3-Chloro-2-fluorophenyl)-2-guanidinoimino)acetonitrile (3.2 g, 0.01 mol) and propan-1-ol (30 ml) were stirred and heated at reflux for 3 h. The cool solution was concentrated in vacuo and the residue chromatographed on silica (250 g). Elution with $CH_2Cl_2$-MeOH (95:5) gave a tan solid. This material was slurried in $CH_2Cl_2$ and the remaining insolubles collected by filtration to give the product (1.3 g) as a cream solid, mp 246-247° C.

$\delta_H$ (500 MHz, dmso-$d_6$) 6.99 (2H, brs, $NH_2$, exchang.), 7.28 (1H, t, J=8 Hz, aromatic H), 7.44 (1H, td, J=8, 2 Hz, aromatic H), 7.65 (1H, td, J=8, 2 Hz, aromatic H), 12.5 (1H, brpeak, NH, exchang.).
m/z 240, 242 ($M^+$+1).

EXAMPLE 36

5(3)-Amino-6-(3-chloro-2-fluorophenyl)-2,3(2,5)-dihydro-3(5)-imino-2-methyl-1,2,4-triazine Iodomethane (0.5 ml, 1.14 g, 8 mmol) was added to a stirred suspension of 3,5-diamino-6-(3-chloro-2-fluorophenyl)-1,2,4-triazine (0.48 g, 2 mmol) in acetone (25 ml). The mixture was stirred at 45° C. for 24 h, cooled, and the solid collected by filtration. Ice (ca. 10 g) was added to the residue followed by 0.88 aqueous ammonia (5 ml) and the mixture stirred for 4 h. The solid was removed by filtration, dried in vacuo and recrystallised from methanol to give 0.23 g of the title compound as an off-white crystalline solid, mp 194-196° C.

$\delta_H$ (500 MHz, dmso-$d_6$) 3.48 (3H, s, $NCH_3$), 6.2-7.2 (2H, vbr peak, $NH_2$, exchang.), 7.27 (1H, t, J=8 Hz, aromatic H), 7.40 (1H, td, J=8, 2 Hz, aromatic H), 7.64 (1H, td, J=8.2 Hz, aromatic H).
m/z 254,256 ($M^+$+1).

EXAMPLE 37

1,1-Dimethylethyl 4-[5(3)-Amino-6-(2,3-dichlorophenyl)-2,3(2,5)-dihydro-3(5)-imino-1,2,4-triazin-2-ylmethyl]piperidine-1-carboxylate or 5(3)-Amino-6-(2,3-dichlorophenyl)-2,3(2,5)-dihydro-3(5)-imino-2-(Bocpiperidin-4-yl)methyl-1,2,4-triazine 1,1-Dimethylethyl 4-iodomethylpiperidine-1-carboxylate [prepared from ethyl isonipecotate by a three step process according to the method of A. Villalobos et al, *J. Med. Chem.*, 37, 2721-2734 (1994)].
(3.25 g, 10 mmol) was added to a stirred suspension of 3,5-diamino-6-(2,3-dichlorophenyl)-1,2,4-triazine (1.28 g, 5 mmol) in acetone (50 ml). The mixture was stirred and heated at reflux for 9 days. After cooling in ice, the solid (2.5 g) was collected by filtration. This material was stirred in water (10 ml) and 0.88 aqueous ammonia (10 ml) for 12 h. The solid was removed by filtration, dried in vacuo and recrystallised from methanol to give 0.60 g of the above urethane as an off-white crystalline solid, of no sharp mp.
m/z 453,455 ($M^+$+1).
$\delta_H$ (500 MHz, dmso-$d_6$) 1.05 (2H, ddd, J=25, 12, 4 Hz, $CCH_2C$), 1.38 (9H, s, $C(CH_3)_3$), 1.59 (2H, brd, J=12 Hz, $CCH_2C$), 2.06 (1H, m, CH), 2.69 (2H, m, $CH_2N$), 3.76 (2H, m, $CH_2N$), 3.92 (2H, brd, J=7 Hz, $NNCH_2$), 5.0-6.0 (1H, vbr peak, NH, exchang.), 6.4-7.0 (2H, vbrpeak, $NH_2$, exchang.), 7.39 (1H, d, J=7.5 Hz, aromatic H), 7.44 (1H, t, J=7.5 Hz, aromatic H), 7.70 (1H, d, J=7.5 Hz, aromatic H).

EXAMPLE 38

4-[5(3)-Amino-6-(2,3-dichlorophenyl)-2,3(2,5)-dihydro-3(5)-imino-1,2,4-triazin-2-ylmethyl]piperidine dimethanesulfonate or 5(3)-Amino-6-(2,3-dichlorophenyl)-2,3(2,5)-dihydro-3(5)-imino-2-(piperidin-4-yl)methyl-1,2,4-triazine 1,1-Dimethylethyl 4-[5(3)-Amino-6-(2,3-dichlorophenyl)-2,3(2,5)-dihydro-3(5)-imino-1,2,4-triazin-2-ylmethyl]piperidine-1-carboxylate (0.5 g, 1.1 mmol) was dissolved in $CH_2Cl_2$ (10 ml) and trifluoroacetic acid (TFA, 10 ml) added. The mixture was stirred for 0.5 h, then concentrated in vacuo. Remaining TFA was removed by azeotroping with toluene. The residue was stirred with saturated $NaHCO_3$ solution (10 ml) and then ammonia (d=0.88) was added until the pH was 12. The mixture was stirred 2 h, the solid which deposited collected by filtration and dried. This material (0.12 g, 0.3 mmol) was dissolved in methanol (3 ml) and methanesulfonic acid (70 mg, 0.7 mmol) added. The solution was stirred for 2 h and then diluted slowly with ether until an oily solid precipitated. This was triturated and removed by filtration and dried in vacuo to give the product (0.18 g) as a off-white solid, mp 180-200° C.
m/z 353,355 ($M^+$+1).
$\delta_H$ (500 MHz, dmso-$d_6$) 1.30 (2H, brddd, J=25, 12, 4 Hz, $CCH_2C$), 1.79 (2H, brd, J=12 Hz, $CCH_2C$), 2.07 (1H, m, CH), 1.59 (2H, brd, J=12 Hz, $CCH_2C$), 2.07 (1H, m, CH), 2.31 (6H, m, $CH_3S$), 2.76 (2H, td, J=12, 4 Hz, $CH_2N$), 3.20 (2H, brd, J=12 Hz, $NCH_2$), 3.22-3.40 (7H, brpeak, NH, exchang.), 4.00 (2H, brd, J=7 Hz, $NNCH_2$), 7.53 (1H, dd, J=7.5, 2 Hz, aromatic H), 7.56 (1H, t, J=7.5 Hz, aromatic H), 7.86 (1H, dd, J=7.5, 2 Hz, aromatic H).

EXAMPLE 39

5(3)-Amino-6-(2,3-dichlorophenyl)-2,3(2,5)-dihydro-3(5)-imino-2-(3,3,3-trifluoropropyl)-1,2,4-triazine no sharp mp (decomp.)
$\delta_H$ (500 MHz, dmso-$d_6$) 2.76-2.86 (2H, m, $CH_2CF_3$), 4.31 (2H, t, J=7 Hz, $NCH_2$), 7.47 (1H, dd, J=8, 1.5 Hz, aromatic H), 7.53 (1H, t, J=8 Hz, aromatic H), 7.84 (1H, dd, J=8, 1.5 Hz, aromatic H), 8.30 (3H, brpeak, NH, exchang.). m/z 352, 354 (M$^+$+1).

EXAMPLE 40

2-chloro-3-fluorophenyl-1,2,4-triazine-3,5-diamine

This compound was prepared in a similar manner to Example 35 via the following intermediates:

Step 1

3-Chloro-2-fluorobenzoic acid was obtained by chlorination of 3-fluorobenzoic acid according to the method of B. Bennetau et al, *J. Chem. Soc. Perkin Trans* 1, 1265-1271 (1995).

Step 2

3-Chloro-2-fluorobenzoyl chloride

Step 3

3-Chloro-2-fluorobenzoyl cyanide

Step 4

2-(3-Chloro-2-fluorophenyl)-2-guanidinoimino)acetonitrile

Step 5

2-chloro-3-fluorophenyl-1,2,4-triazine-3,5-diamine, mp 244-246° C., m/z 240, 242 (M$^+$+1).

$\delta_H$ (500 MHz, dmso-d$_6$) 6.4-7.0 (4H, s+brpeak, 2×NH$_2$, exchang.), 7.25 (1H, m, aromatic H), 7.47 (2H, m, aromatic H).

EXAMPLE 41

3,5-Diamino-6-(2,5-dichlorophenyl)-1,2,4-triazine, mp 228-230° C., was prepared according to the method described in U.S. Pat. No. 4,602,017.

EXAMPLE 42

3,5-Diamino-6-(3,5-dichlorophenyl)-1,2,4-triazine, mp 223-225° C., was prepared from 3,5-dichlorobenzoic acid using similar methodology to that used in Example 33.

EXAMPLE 43

3,5-Diamino-6-phenyl-1,2,4-triazine, mp 218-219° C., was prepared using the method of J. A. Settepani and A. B. Borkovec, *J. Heterocyl. Chem.*, 3, 188-190, (1966)

EXAMPLE 44

3,5-Diamino-6-(2,4-dichlorophenyl)-1,2,4-triazine was prepared according to the method of R. W. A. Rees and P. B. Russell et al, *J. Med. Chem.*, 15, 859-861 (1972).

EXAMPLE 45

5(3)-Amino-6-(2,4-dichlorophenyl)-2,3(2,5)-dihydro-3 (5)-imino-2-methyl-1,2,4-triazine methanesulfonate, mp 283-285° C., was prepared by reaction of 3,5-Diamino-6-(2, 4-dichlorophenyl)-1,2,4-triazine and methyl methanesulfonate in a similar manner to Example 2, but using ethanol as solvent. This compound is described U.S. Pat. No. 4,649, 139.

EXAMPLE 46

5(3)-Amino-6-phenyl-2,3(2,5)-dihydro-3(5)-imino-2-methyl-1,2,4-triazine methanesulfonate, mp 230-232° C., was prepared by reaction of 3,5-Diamino-6-phenyl-1,2,4-triazine and methyl methanesulfonate in a similar manner to that of example 2, but using ethanol as solvent. The free base is described in U.S. Pat. No. 4,649,139.

EXAMPLE 47

5(3)-Amino-6-phenyl-2,3(2,5)-dihydro-3(5)-imino-2-ethyl-1,2,4-triazine methanesulfonate, mp 230-232° C., was prepared by reaction of 3,5-Diamino-6-phenyl-1,2,4-triazine and ethyl methanesulfonate in a similar manner to that of Example 2, but using ethanol as solvent.

EXAMPLE 48

5(3)-Amino-6-(2,5-dichlorophenyl)-2,3(2,5)-dihydro-3 (5)-imino-2-methyl-1,2,4-triazine methanesulfonate, mp 297-298° C., was prepared according to the method described in U.S. Pat. No. 4,649,139.

EXAMPLE 49

5(3)-Amino-6-(2,5-dichlorophenyl)-2,3(2,5)-dihydro-3 (5)-imino-2-ethyl-1,2,4-triazine methanesulfonate, mp 264-265° C., was prepared by reaction of 3,5-Diamino-6-(2,5-dichlorophenyl)-1,2,4-triazine with ethyl methanesulfonate in a similar manner to that described in Example 2, but using ethanol as solvent.

EXAMPLE 50

5(3)-Amino-6-(2,3,5-trichlorophenyl)-2,3(2,5)-dihydro-3 (5)-imino-2-ethyl)-1,2,4-triazine mp 269-271° C., was prepared by reaction of 3,5-Diamino-6-(2,3,5-trichlorophenyl)-1,2,4-triazine with ethyl methanesulfonate in a similar manner to that described in Example 2, but using ethanol as solvent.

EXAMPLE 51

3,5-Diamino-6-(2-trifluoromethoxyphenyl)-1,2,4-triazine, mp 148-150° C., was prepared from 2-trifluoromethoxybenzoic acid using similar methodology to that employed for Example 33

EXAMPLE 52

5(3)-Amino-6-(2,3-dichlorophenyl)-2,3(2,5)-dihydro-3 (5)-imino-2-(2-fluoroethyl)-1,2,4-triazine methanesulfonate

Step 1

2-Fluoroethyl methanesulfonate

Methanesulfonyl chloride (12.6 g, 0.11 mol) was added over 10 min to a stirred solution of 2-fluoroethanol (6.40 g, 0.10 mol) in dichloromethane (100 ml) containing triethylamine (12.1 g, 0.12 mol) kept at 0-5° C. The mixture was stirred for 1 h and allowed to warm to room temperature over this time. The mixture was diluted with dichloromethane (25 ml), and then washed with ice-water (40 ml), followed by cold 10% hydrochloric acid (40 ml), saturated sodium bicarbonate solution (40 ml) and brine (40 ml). The dichloromethane solution was dried over sodium sulfate and the solvent removed in vacuo to give the product as a pale yellow oil (11.4 g). This material was used without further purification for the following reaction.

Step 2

2-fluoroethanol (0.50 g, 3.5 mmol), 3,5-diamino-6-(2,3-dichlorophenyl)-1,2,4-triazine (0.50 g, 2.0 mmol) and dimethylformamide (4 ml) were stirred and heated at 120° C. for 24 h. The solution was cooled, ether (30 ml) added, and the mixture stirred and triturated for 0.5 h. After the mixture settled, the solvent was decanted from the oily precipitate and the residue extracted with boiling 2-butanone (25 ml, 2×) to remove impurities. Crystallisation of the residue from methanol-ether gave the title compound as a light tan solid (0.40 g), mp 253-255° C. (decomp., rapid heating)

$\delta_H$ (500 MHz, dmso-$d_6$) 2.31 (3H, s, SCH$_3$), 4.46 (2H, brdt, J=26.4, 5 Hz, NCH$_2$), 4.76 (2H, brd, J=47.2 Hz, FCH$_2$), 7.55 (2H, m, aromatic H), 7.86 (1H, m, aromatic H), 8.28 (1H, s, NH, exchang.), 8.3-9.0 (2H, vbrpeak, NH$_2$, exchang.), 9.24 (1H, s, NH, exchang.)

EXAMPLE 53

5(3)-Amino-6-(3,5-dichlorophenyl)-2,3(2,5)-dihydro-3 (5)-imino-2-methyl-1,2,4-triazine methanesulfonate, mp 234-236° C., was prepared by reaction of 3,5-Diamino-6-(3, 5-dichlorophenyl)-1,2,4-triazine and methyl methanesulfonate in a similar manner to Example 2, but using ethanol as solvent.

EXAMPLE 54

5(3)-Amino-6-(3,5-dichlorophenyl)-2,3(2,5)-dihydro-3 (5)-imino-2-ethyl-1,2,4-triazine methanesulfonate, mp 217-219° C., was prepared by reaction of 3,5-Diamino-6-(3,5-dichlorophenyl)-1,2,4-triazine and ethyl methanesulfonate in a similar manner to Example 2, but using ethanol as solvent

EXAMPLE 55

5(3)-Amino-6-(2,3,5-trichlorophenyl)-2,3(2,5)-dihydro-3 (5)-imino-2-(2-fluoroethyl)-1,2,4-triazine methanesulfonate, mp 212-214° C., was prepared by reaction of 2-fluoroethyl methanesulfonate with 3,5-diamino-6-(2,3,5-trichlorophenyl)-1,2,4-triazine in dimethylformamide in a similar manner to that of Example 52.

EXAMPLE 56

5(3)-Amino-6-(2,3,5-trichlorophenyl)-2,3(2,5)-dihydro-3(5)-imino-2-(3,3,3-trifluoropropyl)-1,2,4-triazine methanesulfonate Step 1

3,3,3-Trifluoropropyl methanesulfonate was prepared by reaction of 3,3,3-trifluoropropanol with methanesulfonyl chloride by an analogous procedure to that used for Example 52 step 1.

Step 2

Reaction of 3,3,3-trifluoropropyl methanesulfonate with 3,5-diamino-6-(2,3,5-trichlorophenyl)-1,2,4-triazine in dimethylformamide in a similar manner to that of Example 52 gave the title compound of no sharp mp (hygroscopic).

EXAMPLE 57

5(3)-Amino-6-(2,3,dichlorophenyl)-2,3(2,5)-dihydro-3(5)-imino-2-(2,2-difluoroethyl)-1,2,4-triazine Step 1

2,2-Difluoroethyl trifluoromethanesulfonate was prepared by reaction of 2,2-difluoroethanol and triflic anhydride according to the procedure of W. G. Reifenrath et al, *J. Med. Chem.*, 23, 985-990 (1980).

Step 2

2,2-Difluoroethyl trifluoromethanesulfonate (1.40 g, 6.5 mmol) was added to 3,5-diamino-6-(2,3-dichlorophenyl)-1, 2,4-triazine (0.50 g, 2.0 mmol) and dimethylformamide (3.5 ml). The warm mixture was stirred and heated at 100° C. for 2 h and then allowed to stand at room temperature overnight. Ether (35 ml) was added, and the mixture stirred for 0.5 h. After the mixture settled, the solvent was decanted from the oily precipitate and the residue stirred with water (10 ml) and aqueous ammonia solution (5 ml, d=0.88) for 6 h. A tan solid was removed by filtration, washed with water (3 ml) and air-dried. Recrystallisation from propan-2-ol gave the title compound as a light tan solid (0.25 g), mp 179-181° C. (decomp., rapid heating) $\delta_H$ (500 MHz, dmso-$d_6$) 4.30 (2H, brt, J=13.8 Hz, NCH$_2$), 5.6-7.0 (2H, vbrpeak, NH$_2$, exchang.), 6.39 (1H, brt, J=56 Hz, CHF$_2$), 7.3-7.7 (1H, vbrpeak, NH, exchang.), 7.41 (1H, d, J=7.7 Hz, aromatic H), 7.45 (1H, t, J=7.7 Hz, aromatic H), 7.74 (1H, d, J=7.7 Hz, aromatic H).

Biological Testing

Compounds of Formula (I) were tested for various activities as follows:

Screening Strategy:

The screening strategy is designed to select compounds with appropriate sodium channel blocking activity and low side effect liability. To this end all compounds are processed through the primary sodium channel assay (veratrine-evoked uptake of [$^{14}$C]guanidine into rat forebrain synaptosomes) and IC$_{50}$ values computed from generated concentration-effect curves. In order to complement this data IC$_{50}$'s for selected compounds to inhibit binding of [$^3$H]BTX-B are also measured.

Previous studies have shown that substituted triazines are potential inhibitors of DiHydroFolate Reductase (DHFR) activity (McCullough and Bertino 1971, Cashmore et al, 1975, Booth et al, 1987) and Sapse et al, 1994). Inhibitors of DHFR (such as Methotrexate) have been used for the treatment of various cancers (Suster et al, 1978 and Niculescu-Duvaz et al, 1982) as inhibition of this enzyme interferes with cell growth but because of this effect (on cell growth) inhibitors of DHFR may also be teratogenic (Skalko and Gold, 1974, Feldcamp and Carey, 1993 and Buckley et al, 1997). Should compounds be found which are potent inhibitors of DHFR then such compounds may, themselves, have potential as anti-cancer agents. Several methods are available for measurement of inhibition of DHFR activity and for this study we have examined effects of compounds to inhibit the binding of [$^3$H] methotrexate (Myers et al, 1975 and Rothenberg et al, 1977).

Another common side-effect marker is inhibition of human Ether-a-go-go Related Gene potassium (hERG) potassium channel (Inward rectifying, $I_{Kr}$) activity which can be fatal due to heart failure brought about by development of long QT syndrome. A useful preliminary screen to assess potential to affect this channel is assessed by measurement of inhibition of the binding of [$^3$H]astemizole to cell membranes expressing hERG. Selected compounds are tested for this activity by measurement of inhibition @ 10 μM. Assuming inhibition values lie between 10% and 90% it is possible to compute an extrapolated $IC_{50}$ for each compound.

The above screening cascade identifies compounds with appropriate sodium channel blocking activities that have a low(er) propensity for aforementioned side-effect liabilities. In order to develop these compounds further, some knowledge of their pharmacodynamic properties pharmacological action is required.

Sodium channel blockers, such as Sipatrigine, which both reduces the neurological deficit and infarct volume after middle cerebral artery occlusion in rats (Smith et al, 1997) and phenyloin, (which protect retinal ganglion cell death in an experimental model of glaucoma (Hains and Waxman, 2005) show neuroprotective efficacy in a range of models of nerve degeneration. As failure of oxygen supply compromises both glycolysis and oxidative phosphorylation, ischaemic damage ultimately leads to electrical failure (nerve signalling) and pump failure (restoration of cellular membrane potentials). These failures (of electrical and ion pump activity) are associated with decreased local concentrations of ATP (Astrup et al 1981). Thus the effect of compounds to maintain concentrations of ATP in 0.4 mm slices of rat hippocampus following a severe metabolic insult (incubation with the metabolic inhibitor, Iodoacetate) was developed.

Experimental Procedures:
Preparation of Rat Forebrain Synaptosomes and Homogenates:

Experiments were performed using forebrain (whole brain less cerebellum/medulla) from Male Wistar rats weighing 175-250 g. All efforts were made to reduce the number of animals used and all experiments were carried out in accordance with the UK Animals (Scientific Procedures) Act, 1986 and the European Community Council Directive of 24 Nov. 1986 (86/609/EEC). Following killing of animals by stunning and decapitation, the forebrain (whole brain less cerebellum/medulla) was rapidly dissected and transferred to a weighed tube containing ice-cold 0.25M sucrose.

Synaptosomes (heavy and light mitochondrial fraction containing synaptosomes) were prepared by transferring the forebrain (of known wet weight) to a glass Potter vessel to which 9 volumes ice-cold 0.25M sucrose had been added and homogenising, using a teflon pestle, by 8 'up and down strokes' of a Braun Potter S motor driven homogeniser set to 900 rpm. The resulting homogenate was centrifuged at 1036×g at 4° for 10 min and the supernatant collected. The remaining pellet was resuspended, as above, in fresh ice-cold 0.25M sucrose and the centrifugation step repeated. The supernatant fractions were pooled and centrifuged at 40,000×g (average) at 4° for 15 min and the resulting pellet resuspended in the appropriate assay buffer at a concentration of 20-25 mg wet weight per ml appropriate assay buffer.

Homogenates were prepared by transferring the known weight of forebrain to a cooled tube containing 9 volumes of ice-cold 50 mM pH 7.4 HEPES buffer. The mixture was homogenised @ 4° by 3×5 sec bursts of an Ultra-Turrax™ homogeniser set at maximum speed. The resulting homogenate was centrifuged at 40,000×g (average) at 4° for 15 min and the supernatant discarded. The resulting pellet was resuspended in 9 volumes of fresh ice-cold pH 7.4 buffer (as above), the centrifugation step was repeated and the resulting pellet resuspended in the [$^3$H]BTX-B binding buffer at a concentration of 20-25 mg wet weight per ml assay buffer.

[$^{14}$C]Guanidine Flux and Binding of [$^3$H]BTX-B:

Both assays were carried out using 14 ml polypropylene test tubes to which a range of concentrations of the compounds under test were added. Test compounds were dissolved in DMSO and added to assays such that maximum concentration of DMSO did not exceed 2% v/v.

[$^{14}$C]Guanidine Flux:

Compounds under test were pre-incubated for 10 min at 30° in incubation buffer (50 mM pH 7.4 HEPES (adjusted to pH 7.4 with Tris base), 130 mM choline chloride, 5.5 mM D-glucose, 0.8 mm $MgSO_4$ and 5 mM KCl) containing 7.5 mg original wet weight of tissue and 100 μg veratrine HCl in a final volume of 0.5 ml. Uptake was initiated by the addition of 0.5 ml of [$^{14}$C]guanidine (1.0 μCi/ml in incubation buffer) and terminated 2.5 min later by the addition of 10 ml of ice-cold wash buffer (163 mM choline chloride, 1.8 mM $CaCl_2$ and 0.8 mM $MgSO_4$ in 5 mM pH 7.4 HEPES buffer), followed immediately by vacuum filtration through Whatman GF/C glass fibre filters using a Brandel™ cell harvester. A further 2×5 ml of ice-cold wash buffer was added to each tube and the vacuum filtration step repeated. The GF/C glass fibre filters were transferred to minivials and 4 ml Picofluor[40] liquid scintillant added using a Brandel™ deposit/dispense system. Radioactivity was measured using a Beckman Liquid Scintillation Counter.

Binding of [3H]BTX-B:

Binding was initiated by the addition of 5 mg original wet weight of tissue to tubes containing [$^3$H] BTX-B (incubation concentration measured independently by measurement of radioactivity), drug under test and 25 μg α-scorpion venom in a final volume of 0.25 ml of incubation buffer (see above but modified to contain 134 mM choline chloride and 1 mM KCl). Samples were mixed, incubated for 90 minutes @ 25° and assays terminated by the addition of 5 ml of ice-cold wash buffer (see above), followed immediately by vacuum filtration through Whatman GF/C glass fibre filters using a Brandel™ cell harvester. A further 5 ml of ice-cold wash buffer was added to each tube and the vacuum filtration step repeated. The GF/C glass fibre filters were transferred to minivials and 4 ml Picofluor[40] liquid scintillant added using a Brandel™ deposit/dispense system. Radioactivity was measured using a Beckman Liquid Scintillation Counter and cpm converted directly to dpm via reference to appropriate quench parameters.

Binding of [3H]Methotrexate

All steps were carried out at 4° (or on ice). Freshly dissected rat liver was dissected into 0.25M ice-cold Sucrose and subsequently homogenised (U-turrax) in 50 mM pH 6.0 phosphate buffer (10 ml/g tissue) containing 15 mM Dithiothreitol. The resulting homogenate was centrifuged @ 47,500×g for 20 min and supernatant (filtered through cotton wool to remove fatty lumps) stored @-80° before use (Rothenberg et al).

Inhibition of the binding of [$^3$H]methotrexate to rat liver homogenate supernatant fractions were carried out essentially as described by Arons et al, 1975. Briefly compounds were incubated with NADPH (480 μM), liver supernatant (DHFR enzyme) and [$^3$H]metotrexate (50 nM) in a final volume of 410 μL of 50 mM pH 6.0 phosphate buffer in the presence of Mercaptoethanol (60 mM) for 15 minutes at room temperature. The binding reaction was stopped by the addition of 50 µl of a charcoal suspension (consisting of charcoal, Bovine Serum Albumin and Dextran present in a weight ratio of 100:4:1 suspended in 50 mM pH 6.0 phosphate buffer. Samples were vortexed, allowed to stand for 2 minutes and charcoal was precipitated by microcentrifugation @ full speed for 5 min. Aliquots of clear supernatant were transferred to counting vials containing liquid scintillant for measurement of radioactivity using Liquid Scintillation Spectroscopy.

Specific binding of [$^3$H]methotrexate was determined as the difference in binding in the presence and absence of 200 µM 'cold' methotrexate. Percentage inhibition values were calculated by comparison to this value.

Computation of IC$_{50}$ Values:

Data are presented as mean±sem of number of experiments indicated in brackets. IC$_{50}$ values were obtained from radioligand displacement or guanidine flux inhibition curves by plotting log$_{10}$ concentration vs bound ligand/guanidine uptake according the equation:—

$$y = R\min + Rsp/\{1+\exp[-n(x-C)]\}$$

where
  y=bound (dpm)
  x=log$_{10}$ compound concentration
  Rmin=lower asymptote (i.e. 100% inhibition)
  Rsp=upper asymptote−Rmin (i.e. specific binding)
  n=slope (loge)
  and C=IC$_{50}$ (i.e. concentration required to inhibit 50% of specific binding)

Hippocampal Slice Assay:

Following killing of animals by stunning and decapitation, the forebrain (whole brain less cerebellum/medulla) was rapidly dissected and transferred to a vessel containing ice-cold pre-gassed artificial cerebral spinal fluid (aCSF). Hippocampi were rapidly dissected and 0.4 mm slices prepared using a McIlwain tissue chopper. Slices were randomly distributed in 50 ml conical flasks containing 25-30 ml ice-cold pre-gassed aCSF. Flasks were incubated @ 30° for 30 minutes under continued gassing with 95% O$_2$/5% CO$_2$ when medium was removed by vacuum aspiration. Fresh aCSF was added and slices were incubated for a further 30 minutes as described previously. Medium was again removed by vacuum aspiration and replaced by 25 ml of pre-warmed (30°) Ca$^{2+}$-free aCSF. Following a further 10 min incubation under continuous gassing 2-3 slices were removed (in a volume of 100 µl using an Eppendorf pipette) for measurement of ATP and protein by immediate transfer to individual microfuge tubes containing 0.4 ml of ice-cold 0.5M TriChloroacetic Acid (TCA) Iodoacetate (25 µl of an 0.4 M solution) was added to flask and gassing discontinued. Exactly 11 min later 3-4 slices were removed and transferred to microfuge tubes as described previously.

Measurement of ATP and Protein:

Individual slices were disrupted by ultra-sonication and the resulting homogenates centrifuged @ 10000×g for 5 min @ 4°. The supernatant was decanted into a fresh tube and any remaining supernatant removed by vacuum aspiration. The pellet was resuspended in 0.5 ml 0.1M KOH by ultra-sonication and the resulting suspensions warmed with gentle agitation @ 37° for 30 minutes.

Concentrations of ATP were measured in 6 µl of supernatant by mixing with Luciferase reagent (ATPLite from Perkin Elmer) and measuring subsequent luminescence in a 96-well plate Counter.

Protein concentration was measured using BCA™ protein assay (Pierce) with Bovine Serum albumin as reference standard.

ATP concentrations were expressed as nmoles/mg protein and neuroprotective indices (% protection) calculated by direct comparison with the effect of 1 µM TTX.

hERG:

Assays were carried out to measure effects of compounds @ 10 µM. Making the assumption that binding slopes would be 1 and for compounds with inhibition values between 10% and 90% IC$_{50}$ values were extrapolated.

Results:

TABLE 1

| Compound | [$^{14}$C] guanidine uptake (synaptosomes) | [$^3$H]BTX-B binding (synaptosomes) |
|---|---|---|
| Lamotrigine | 186.5 ± 26.5 (5) | 82.6 ± 2.3 (3) |
| N-methyl-lamotrigine | 35.9 ± 1.8 (3) | 7.4 ± 0.4 (2) |
| BW202W92 | 2.0 ± 0.2 (9) | 4.5 ± 0.4 (4) |

Data presented as mean IC$_{50}$ (µM) ± sem of the number of experiments indicated in brackets

TABLE 2

Compound nomenclatures and structures:

| Example | Ring substituents | N-subst |
|---|---|---|
| 1 | 2',3'-dichloro | H |
| 2 | 2',3'-dichloro | Methyl |
| 3 | 2',3'-dichloro | Ethyl |
| 4 | 2',3'-dichloro | Iso-propyl |
| 5 | 2',3'-dichloro | Hydroxy-ethyl |
| 6 | 2',3'-dichloro | n-Propyl |
| 7 | 2',3'-dichloro | Iso-butyl |
| 8 | 2',3'-dichloro | n-Butyl |
| 9 | 2',3'-dichloro | Benzyl |
| 10 | 2',3'-dichloro | Allyl |
| 11 | 2',3'-dichloro | Carboxamido |
| 12 | 2',3'-dichloro | 4'-Me-benzyl |
| 13 | 2',3'-dichloro | 2',3' di-F-benzyl |
| 14 | 2',3'-dichloro | 2'-F-benzyl |
| 15 | 2',3'-dichloro | 3'-F-benzyl |
| 16 | 2',3'-dichloro | 4'-F-benzyl |
| 17 | 2',3'-dichloro | 2'-OMe-benzyl |
| 18 | 2',3'-dichloro | 3'-OMe-benzyl |
| 19 | 2',3'-dichloro | 4'-OMe-benzyl |
| 20 | 2',3'-dichloro | 3'-Cl-benzyl |
| 21 | 2',3'-dichloro | 4'-Cl-benzyl |
| 22 | 2',3'-dichloro | 2'-Cl-benzyl |
| 23 | 2',3'-dichloro | 2'-CF$_3$-benzyl |
| 24 | 2',3'-dichloro | 3'-CF$_3$-benzyl |
| 25 | 2',3'-dichloro | 4'-CF$_3$-benzyl |
| 26 | 2',3'-dichloro | 2'-F,3'-CF$_3$-benzyl |
| 27 | 2',3'-dichloro | 4'-CONH$_2$-benzyl |
| 28 | 2',3'-dichloro | 4'-CH$_2$OH-benzyl |
| 29 | 2',3'-dichloro | Thienyl |
| 30 | 2',3'-dichloro | Furyl |
| 31 | 2',3',5'-trichloro | H |
| 32 | 2',3',5'-trichloro | Methyl |
| 33 | 2',3'-difluoro | H |
| 34 | 2',3',5'-trichloro | Propyl |
| 35 | 2-F', 3'-Cl | H |
| 36 | 2-F', 3'-Cl | Methyl |
| 37 | 2',3'-dichloro | 2-BocPiperidCH$_2$ |
| 38 | 2',3'-dichloro | 2-PiperidCH$_2$ |
| 39 | 2',3'-dichloro | CH$_2$CH$_2$CF$_3$ |
| 40 | 3'-F, 2'-Cl | H |
| 41 | 2',5'-dichloro | H |
| 42 | 3',5'-dichloro | H |
| 43 | Des-chloro | H |
| 44 | 2',4'-dichloro | H |
| 45 | 2',4'-dichloro | Methyl |
| 46 | Des-chloro | Methyl |
| 47 | Des-chloro | Ethyl |

TABLE 2-continued

Compound nomenclatures and structures:

| Example | Ring substituents | N-subst |
|---|---|---|
| 48 | 2',5'-dichloro | Methyl |
| 49 | 2',5'-dichloro | Ethyl |
| 50 | 2',3',5'-trichloro | Ethyl |
| 51 | 2'-OCF$_3$ | H |
| 52 | 2',3'-dichloro | F-ethyl |
| 53 | 3',5'-dichloro | Methyl |
| 54 | 3',5'-dichloro | Ethyl |
| 55 | 2',3',5'-trichloro | F-ethyl |
| 56 | 2',3',5'-trichloro | 3,3,3,-triF-propyl |
| 57 | 2',3'-dichloro | 2,2-diF-ethyl |

TABLE 3

[$^{14}$C]guanidine flux summary

| Compound | Mean (IC50: μM) | Sem | n |
|---|---|---|---|
| Sipatrigine | 13.1 | 1.3 | 10 |
| BW202W92 | 2.0 | 0.2 | 9 |
| Lamotrigine | 208.9 | 38.0 | 7 |
| 2 | 35.9 | 1.8 | 3 |
| 3 | 6.4 | 0.4 | 2 |
| 4 | 4.0 | 0.5 | 2 |
| 5 | 172.2 | 46.2 | 4 |
| 6 | 2.8 | 0.5 | 4 |
| 7 | 2.9 | 0.3 | 2 |
| 8 | 2.1 | 0.2 | 2 |
| 9 | 4.8 | 0.4 | 4 |
| 10 | 6.1 | 2.6 | 2 |
| 11 | >100 | — | 2 |
| 12 | 4.1 | 0.5 | 2 |
| 13 | 2.8 | 0.0 | 2 |
| 14 | 2.8 | 0.6 | 2 |
| 15 | 3.9 | 0.3 | 2 |
| 16 | 5.1 | 0.6 | 2 |
| 17 | 4.6 | 0.3 | 2 |
| 18 | 3.1 | 0.1 | 2 |
| 19 | 5.0 | 0.6 | 2 |
| 20 | 3.5 | 0.1 | 2 |
| 21 | 6.5 | 0.6 | 2 |
| 22 | 4.6 | — | 1 |
| 23 | 4.4 | — | 1 |
| 24 | 4.0 | — | 1 |
| 25 | 6.2 | — | 1 |
| 26 | 5.3 | — | 1 |
| 27 | 234.4 | — | 1 |
| 28 | 49.0 | — | 1 |
| 29 | 7.3 | 1.0 | 2 |
| 30 | 4.4 | 0.2 | 2 |
| 31 | 16.2 | 3.3 | 2 |
| 32 | 6.4 | 0.4 | 2 |
| 33 | >300 | — | 2 |

TABLE 3-continued

[$^{14}$C]guanidine flux summary

| Compound | Mean (IC50: μM) | Sem | n |
|---|---|---|---|
| 34 | 1.3 | — | 1 |
| 35 | 489.8 | — | 1 |
| 36 | 128.8 | — | 1 |
| 37 | 12.9 | — | 1 |
| 38 | 20.9 | — | 1 |
| 39 | 3.9 | 0.3 | 2 |
| 40 | 834.5 | 142.7 | 2 |
| 41 | 524.9 | — | 1 |
| 42 | 154.9 | — | 1 |
| 43 | >500 | — | 1 |
| 44 | 603.0 | — | 1 |
| 45 | 87.1 | — | 1 |
| 46 | 2291.0 | — | 1 |
| 47 | 676.0 | — | 1 |
| 48 | 28.2 | — | 1 |
| 49 | 20.9 | — | 1 |

TABLE 4

[$^3$H]BTX-B binding summary

| Example | Assay | Tissue prep'n | Mean (IC50: μM) | Sem | n |
|---|---|---|---|---|---|
| Sipatrigine | [$^3$H]BTX-B | Synaptosomes | 4.9 | 0.7 | 4 |
|  | [$^3$H]BTX-B | Homogenate | 9.4 | 2.8 | 3 |
| BW202W92 | [$^3$H]BTX-B | Synaptosomes | 4.5 | 0.4 | 4 |
|  | [$^3$H]BTX-B | Homogenate | 4.1 | 0.6 | 5 |
| Lamotrigine | [$^3$H]BTX-B | Synaptosomes | 76.6 | 6.2 | 5 |
|  | [$^3$H]BTX-B | Homogenate | 97.9 | 37.7 | 3 |
| 2 | [$^3$H]BTX-B | Synaptosomes | 7.2 | 0.8 | 4 |
|  | [$^3$H]BTX-B | Homogenate | 2.5 | 1.3 | 3 |
| 3 | [$^3$H]BTX-B | Synaptosomes | 3.7 | 0.6 | 2 |
|  | [$^3$H]BTX-B | Homogenate | 0.9 | — | 1 |
| 4 | [$^3$H]BTX-B | Synaptosomes | 1.5 | 0.2 | 2 |
|  | [$^3$H]BTX-B | Homogenate | 0.6 | — | 1 |
| 5 | [$^3$H]BTX-b | Synaptosomes | 25.7 | — | 1 |
|  | [$^3$H]BTX-b | Homogenate | 7.2 | — | 1 |
| 6 | [$^3$H]BTX-B | Synaptosomes | 3.6 | 1.3 | 2 |
|  | [$^3$H]BTX-B | Homogenate | 0.5 | — | 1 |
| 7 | [$^3$H]BTX-B | Synaptosomes | 1.0 | — | 1 |
| 8 | [$^3$H]BTX-B | Synaptosomes | 1.7 | — | 1 |
| 9 | [$^3$H]BTX-B | Synaptosomes | 2.2 | — | 1 |
| 29 | [$^3$H]BTX-B | Synaptosomes | 2.2 | — | 1 |
| 30 | [$^3$H]BTX-B | Synaptosomes | 2.6 | — | 1 |
| 31 | [$^3$H]BTX-B | Synaptosomes | 21.9 | — | 1 |
| 32 | [$^3$H]BTX-B | Synaptosomes | 1.9 | — | 1 |
| 34 | [$^3$H]BTX-B | Synaptosomes | 0.5 | — | 1 |
| 39 | [$^3$H]BTX-B | Synaptosomes | 1.6 | — | 1 |
| 40 | [$^3$H]BTX-B | Synaptosomes | 282.8 | — | 1 |

TABLE 5

Extrapolated IC$_{50}$'s (hERG) from single point inhibition study and [K] (hERG):[Na] channel selectivities MDS Results

| Example | hERG % inhibition @ 10 μM | hERG Extrapolated IC$_{50}$ (μM) | [$^{14}$C]guanidine flux IC$_{50}$ (μM) | [$^3$H]BTX-B* IC$_{50}$ (μM) | hERG [$^{14}$C]guanidine flux | hERG [$^3$H]BTX-B |
|---|---|---|---|---|---|---|
| Sipatrigine | 87 | 1.5 | 13.1 | 4.9 | 0.1 | 0.3 |
| 1 | 1 | >900 | 208.9 | 76.6 | >4.3 | >11.7 |
| 2 | 12 | 73.3 | 35.9 | 7.2 | 2.0 | 10.2 |
| 3 | 32 | 21.2 | 6.4 | 3.7 | 3.3 | 5.7 |
| 3 | 36 | 17.8 | 4.0 | 1.5 | 4.5 | 11.9 |
| 4 | 35 | 18.6 | 2.8 | 3.6 | 6.6 | 5.2 |
| 4 | 34 | 19.4 | 2.9 | 1.0 | 6.7 | 19.4 |
| 5 | 58 | 7.2 | 2.1 | 1.7 | 3.5 | 4.3 |

TABLE 5-continued

Extrapolated IC$_{50}$'s (hERG) from single point inhibition study and [K] (hERG): [Na] channel selectivities
MDS Results

| Example | hERG % inhibition @ 10 µM | hERG Extrapolated IC$_{50}$ (µM) | [$^{14}$C]guanidine flux IC$_{50}$ (µM) | [$^3$H]BTX-B* IC$_{50}$ (µM) | hERG [$^{14}$C]guanidine flux | hERG [$^3$H]BTX-B |
|---|---|---|---|---|---|---|
| 6 | 78 | 2.8 | 4.8 | 2.2 | 0.6 | 1.3 |
| 14 | 80 | 2.5 | 2.8 | nd | 0.9 | — |
| 15 | 83 | 2.0 | 3.9 | nd | 0.5 | — |
| 13 | 84 | 1.9 | 2.8 | nd | 0.7 | — |
| 17 | 84 | 1.9 | 4.6 | nd | 0.4 | — |
| 18 | 87 | 1.5 | 3.1 | nd | 0.5 | — |
| 23 | 90 | 1.1 | 4.4 | nd | 0.3 | — |
| 24 | 94 | 0.6 | 4.0 | nd | 0.2 | — |
| 10 | 50 | 10.0 | 6.1 | nd | 1.6 | — |
| 29 | 83 | 2.0 | 7.3 | 2.2 | 0.3 | 0.9 |
| 30 | 65 | 5.4 | 4.4 | 2.6 | 1.2 | 2.1 |
| 31 | 13 | 66.9 | 16.2 | 21.9 | 4.1 | 3.1 |
| 32 | 33 | 20.3 | 6.4 | 1.9 | 3.2 | 10.7 |
| 34 | 62 | 6.1 | 1.3 | 0.5 | 4.7 | 12.3 |
| 36 | 33 | 20.3 | 128.8 | nd | 0.2 | — |
| 38 | 80 | 2.5 | 20.9 | nd | 0.1 | — |
| 39 | 40 | 15.0 | 3.9 | 1.6 | 3.8 | 9.4 |

*Synaptosome data

TABLE 6

Summary of [$^3$H]methotrexate binding data

| Examples | Assay concentration (µM) | IC$_{50}$ (µM) | Inhibition (%* @ assay conc'n) | n |
|---|---|---|---|---|
| Methotrexate | — | 18 ± 0.08 nM | — | 4 |
| Pyrimethamine | — | 2.8 | — | 1 |
| Trimethoprim | — | 955 | — | 1 |
| BW202W92 | 10 | — | −1 | 1 |
| | 99 | — | 29 | 1 |
| Sipatrigine | 10 | — | 0 | 1 |
| | 198 | — | −6 | 1 |
| 1 (Lamotrigine) | — | 770 ± 96 | — | 3 |
| | 10 | — | −1.5 ± 0.5 | 2 |
| | 99 | — | 11 | 1 |
| 2 | 10 | — | 0 | 1 |
| | 99 | — | −3 | 1 |
| 3 | 10 | — | 0 | 1 |
| | 99 | — | 1 | 1 |
| 4 | 10 | — | −1 | 1 |
| | 99 | — | 0 | 1 |
| 5 | 10 | — | −1 | 1 |
| | 101 | — | 1 | 1 |
| 6 | 10 | — | 0 | 1 |
| | 99 | — | 2 | 1 |
| 7 | 10 | — | −4 | 1 |
| | 99 | — | −2 | 1 |
| 8 | 10 | — | −4 | 1 |
| | 99 | — | −2 | 1 |
| 9 | 10 | — | 2 | 1 |
| | 99 | — | −4 | 1 |
| 10 | 10 | — | −2 | 1 |
| | 99 | — | −1 | 1 |
| 11 | 20 | — | −3 | 1 |
| | 99 | — | −3 | 1 |
| 12 | 20 | — | −2 | 1 |
| | 99 | — | −3 | 1 |
| 13 | 10 | — | −3 | 1 |
| | 99 | — | −4 | 1 |
| 14 | 10 | — | −1 | 1 |
| | 99 | — | −4 | 1 |
| 15 | 10 | — | −4 | 1 |
| | 99 | — | −5 | 1 |
| 16 | 10 | — | −3 | 1 |
| | 99 | — | −3 | 1 |
| 17 | 10 | — | −4 | 1 |
| | 198 | — | −3 | 1 |
| 18 | 10 | — | −4 | 1 |
| | 99 | — | −5 | 1 |
| 19 | 10 | — | −2 | 1 |
| | 99 | — | −3 | 1 |
| 20 | 9 | — | −4 | 1 |
| | 99 | — | −7 | 1 |
| 21 | 10 | — | −4 | 1 |
| | 95 | — | −4 | 1 |
| 29 | — | >250 | — | 1 |
| 30 | — | >250 | — | 1 |
| 31 | — | 41.0 ± 4.7 | — | 2 |
| 32 | — | >250 | — | 2 |
| 33 | — | 441.6 ± 5.1 | — | 2 |
| 34 | — | >300 | — | 1 |
| 35 | — | 81.3 | — | 1 |
| 36 | — | >300 | — | 1 |
| 37 | — | >300 | — | 1 |
| 38 | — | >300 | — | 1 |
| 39 | — | >300 | — | 1 |
| 40 | — | 589 | — | 1 |
| 41 | 50 | — | 93 | 1 |
| 42 | 50 | — | 99 | 1 |
| 43 | 50 | — | 82 | 1 |
| 44 | — | 105 | — | 1 |
| 45 | 495 | — | −1 | 1 |
| 46 | — | 288 | — | 1 |
| 47 | 495 | — | 1 | 1 |
| 48 | — | 251 | — | 1 |
| 49 | — | 95 | — | 1 |

*% inhibition computed from methotrexate displacement curve

TABLE 7

Summary of hippocampal slice data

| Example | EC$_{50}$ (µM) | Max Protection (% v TTX^) | EC$_{50}$ (+max set @ 100) |
|---|---|---|---|
| Sipatrigine | 10.7 | 90.0 | 12.6 |
| 1 (Lamotrigine) | 30.2 | 79.0 | 33.1 |
| 2 | 36.3 | 98 ± 5 | 37.4 |

TABLE 7-continued

Summary of hippocampal slice data

| Example | EC$_{50}$ (μM) | Max Protection (% v TTX^) | EC$_{50}$ (+max set @ 100) |
|---|---|---|---|
| 3 | 16.0 | 87.0 | 20.0 |
| 6 | 10.4 | 81 ± 27 | 14.5 |
| 7 | 1.3* | 47 ± 3 | — |
| 8 | 10.0 | 46.0 | — |
| 9 | >>30 | — | — |
| 31 | 1.8 | 91 ± 4 | 2.2 |
| 32 | 5.9 | 65 ± 7 | — |
| 34 | 9.8 | 37.0 | — |

*slope set to 2.30
^[ATP] in presence of 1 μM TTX was 71.8 ± 2.9% (17) as compared with untreated control (pre-IOAA slices) = 100% protection.
+if max approaches 100% then data re-computed setting max @ 100%

TABLE 8

Effect of compounds on uptake of [14C]guanidine

| Compound | Rmin | % Specific | Hill | pIC50 | IC50 (μM) |
|---|---|---|---|---|---|
| Lamotrigine | 1968 ± 597 | 72.9 | 0.93 | 3.75 ± 0.13 | 177.8 |
|  | 1934 ± 990 | 72.0 | 0.71 | 3.68 ± 0.27 | 208.9 |
| BW202W92 | 3019 ± 70 | 55.9 | 1.07 | 5.61 ± 0.04 | 2.5 |
| 50 | 2616 ± 91 | 66.8 | 0.93 | 5.52 ± 0.03 | 3.0 |
| 51 | 2026 ± 27 | 72.2 | 1.22 | 2.76 ± 0.11 | 1737.8 |
| 52 | 2472 ± 197 | 64.9 | 0.74 | 5.00 ± 0.08 | 10.0 |
| 53 | 2009 ± 575 | 72.2 | 0.73 | 4.34 ± 0.16 | 45.7 |
| 54 | 2297 ± 316 | 65.7 | 0.76 | 4.73 ± 0.11 | 18.6 |
| 55 | 2209 ± 122 | 67.9 | 0.79 | 5.20 ± 0.05 | 6.31 |
| 56 | 1807 ± 107 | 72.9 | 0.83 | 2.90 ± 0.20 | 1258.9 |

REFERENCES

McCullough, J. L., and Bertino, R. (1971) Biochem Pharmacol 20(3): 561-74.

Cashmore, A. R., Skeel, R. T., Makulu, D. R., Gralla, E. J. and Bertino, J. R. (1975) Cancer Res 35(1): 17-22.

Booth, R. G., Selassie, C. D., Hansch, C. and Santi, D. V. (1987) J Med Chem 30(7): 1218-24.

Sapse, A. M., Waltham, M. C. and Bertino, J. R. (1994) Cancer Invest 12(5): 469-76.

Niculescu-Duvaz, I., Ciustea, G., Stoicescu, D., Muresan, Z. and Dobre, V. (1982) Neoplasma 29(1): 43-52.

Suster, D. C., Tarnauceanu, E., Botez, G., Dobre, V. and Niculescu-Duvaz, I. (1978) J Med Chem 21(11): 1165-7

Skalko, R. G. and Gold, M. P. (1974) Teratology 9(2):159-63.

Feltkamp, M. and Carey, J. C. (1993) Teratology 47(6): 533-9.

Buckley, L. M., Bullaboy, C. A., Leichtman, L. and Marquez, M. (1997) Arthritis Rheum 40(5): 971-3.

Rothenberg, S. P., da Costa, M. and Iqbal, M. P. (1977) Cancer Treat Rep 61: 575-84.

Arons, E., Rothenberg, S. P., da Costa, M., Fischer, C. and Iqbal, M. P. (1975) Cancer Research 35: 2033-38

The invention claimed is:

1. Method for the treatment of epilepsy, multiple sclerosis, glaucoma and uevitis, cerebral traumas and cerebral ischaemias, stroke, head injury, spinal cord injury, surgical trauma, motorneurone disease, Alzheimer's disease, Parkinson's disease, chronic inflammatory pain, neuropathic pain, migraine, bipolar disorder, anxiety, schizophrenia or trigeminal autonomic cephalalgias in a patient suffering from one of said disorders, comprising administering to said patient an effective amount of a compound of formula (I):

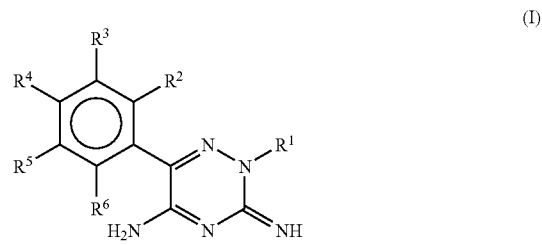

(I)

or a salt or solvate thereof, in which
$R^1$ is $C_{2-10}$ alkenyl, $C_{1-3}$ alkylaryl, $C_{1-3}$ alkyl-heterocyclyl, hydroxyalkyl, carboxamido or $C_{3-10}$ cycloalkyl, any of which is optionally substituted by one or more of: halogen, halo $C_{1-6}$ alkyl, $C_{1-6}$ alkyl, hydroxyalkyl, carboxamido or $C_{1-6}$ alkoxy;
$R^2$ to $R^6$ are independently selected from hydrogen, halogen, $C_{1-6}$ alkyl, alkenyl, alkynyl or alkoxy, amino, mono- or di-substituted amino, alkenyloxy, acyl, acyloxy, cyano, nitro, aryl and alkylthio groups.

2. Method according to claim 1, in which
$R^2$ is selected from halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups; and
$R^3$ to $R^6$ are independently selected from hydrogen, halogen, $C_{1-6}$ alkyl, alkenyl, alkynyl or alkoxy, amino, mono- or di-substituted amino, alkenyloxy, acyl, acyloxy, cyano, nitro, aryl and alkylthio groups.

3. Method according to claim 1, in which $R^1$ is hydroxyalkyl, alkyl-heterocyclyl, alkenyl, carboxamido, benzyl, benzyl substituted by one or more of: halogen, alkyl, alkoxy, hydroxyalkyl, haloalkyl or carboxamido; and $R^2$ to $R^6$ are independently selected from hydrogen and halogen.

4. Method according to claim 1, in which the compound of formula (I) is
5-amino-6-(2,3-dichlorophenyl)-2,3-dihydro-3-imino-2-benzyl-1,2,4-triazine or
5-amino-6-(2,3-dichlorophenyl)-2,3-dihydro-3-imino-2-allyl-1,2,4-triazine.

* * * * *